United States Patent [19]
Jepson et al.

[11] Patent Number: 5,957,898
[45] Date of Patent: Sep. 28, 1999

[54] NEEDLELESS CONNECTOR

[75] Inventors: Steven C. Jepson; Thomas E. Dudar, both of Palatine; Rodrigo A. Montanez, Waukegan; Algirdas J. Bindokas, Clarendon Hills, all of Ill.; Michael J. Finley, Wilmot, Wis.; Jason J. White, Chicago, Ill.; Camille Summer, Crystal Lake, Ill.; Samuel Ding, Vernon Hills, Ill.; Lewis E. Daniels, Wonder Lake, Ill.

[73] Assignee: Baxter International Inc., Deerfield, Ill.

[21] Appl. No.: 09/081,728

[22] Filed: May 20, 1998

Related U.S. Application Data

[60] Provisional application No. 60/047,161, May 20, 1997.

[51] Int. Cl.⁶ ................................................. A61M 5/00
[52] U.S. Cl. ............................ 604/256; 604/283; 128/912
[58] Field of Search ................................. 604/246, 167, 604/201, 203, 236, 237, 244, 245, 256, 283, 411, 415; 128/912; 251/334

[56] References Cited

U.S. PATENT DOCUMENTS

| | | |
|---|---|---|
| D. 321,250 | 10/1991 | Jepson et al. . |
| D. 321,251 | 10/1991 | Jepson et al. . |
| 808,026 | 12/1905 | Dunn . |
| 811,811 | 2/1906 | Allison . |
| 1,180,665 | 4/1916 | McElroy . |
| 1,578,517 | 3/1926 | Hein . |
| 2,289,677 | 7/1942 | Perelson . |
| 2,387,512 | 10/1945 | Hilberg . |
| 2,579,724 | 12/1951 | Breakstone . |
| 2,594,405 | 4/1952 | Deters . |
| 2,653,606 | 9/1953 | Ryan . |
| 2,682,874 | 5/1954 | Hickey . |
| 2,707,953 | 5/1955 | Ryan . |
| 2,847,995 | 8/1958 | Adams . |
| 2,881,937 | 4/1959 | Roberts . |
| 2,899,975 | 8/1959 | Fernandez . |
| 2,933,333 | 4/1960 | Bredtschnieder . |

(List continued on next page.)

FOREIGN PATENT DOCUMENTS

| | | |
|---|---|---|
| 1105959 | 7/1981 | Canada . |
| 2083670 | 5/1993 | Canada . |
| 0 051 718 | 5/1982 | European Pat. Off. . |
| 0 111 723 | 11/1983 | European Pat. Off. . |
| 0114677 | 8/1984 | European Pat. Off. . |
| 0 223 451 | 5/1987 | European Pat. Off. . |

(List continued on next page.)

OTHER PUBLICATIONS

*Machinery's Handbook,* 23rd Edition, by Erik Oberg, Franklin D. Jones and Holbrook L. Horton., pp. 1610–1621.

Conical Fittings with a 6% (Luer) taper for Syringes, Needles and Certain Other Medical Equipment—Part 1 general Requirments, *International Standard,* ISO 594/1, First Edition, Jun. 15, 1986, pp. 1–7.

Amplatz Extra Stiff Wire Guides, T.P. Smith, M.D. Darcey, D.W. Hunter, W.R. Casaneda–Zuniga, K. Amplatz; Raidology, 161, 1986, pp. 551–552.

(List continued on next page.)

*Primary Examiner*—Wynn Wood Coggins
*Assistant Examiner*—Sharon Finkel
*Attorney, Agent, or Firm*—Jeffrey C. Nichols; Mark J. Bounaiuto; Francis C. Kowalik

[57] ABSTRACT

A needless connector is provided which utilizes a resealable preslit septum valve. The valve is resiliently restrained relative to a housing with the valve and housing configured to accept a standard male luer lock having a luer tip which penetrates the valve through the opening to extend within the housing and a luer locking flange of the luer lock extending about the housing. The valve includes a disk shaped upper portion covering the opening, a lower portion spaced from the housing and extending downward from the disk shaped portion into a passageway defined by the housing, and an annular skirt to attach the septum to the housing. The connector exhibits satisfactory leak pressure after multiple connections and disconnects to the luer lock fitting and long periods of indwell of the luer tip.

10 Claims, 14 Drawing Sheets

U.S. PATENT DOCUMENTS

| | | | |
|---|---|---|---|
| 2,999,499 | 9/1961 | Willet . | |
| 3,057,350 | 10/1962 | Cowley . | |
| 3,067,425 | 12/1962 | Colley | 604/256 |
| 3,084,688 | 4/1963 | McConnaughey . | |
| 3,091,240 | 5/1963 | McConnaughey et al. . | |
| 3,134,380 | 5/1964 | Armao . | |
| 3,157,201 | 11/1964 | Littmann . | |
| 3,200,860 | 8/1965 | Barton et al. . | |
| 3,308,798 | 3/1967 | Snider . | |
| 3,354,881 | 11/1967 | Bloch . | |
| 3,416,567 | 12/1968 | Dardel et al. . | |
| 3,434,869 | 3/1969 | Davidson . | |
| 3,466,065 | 9/1969 | Acker et al. . | |
| 3,570,484 | 3/1971 | Steer et al. . | |
| 3,601,151 | 8/1971 | Winnard . | |
| 3,620,500 | 11/1971 | Santomieri . | |
| 3,648,684 | 3/1972 | Barnwell et al. . | |
| 3,663,288 | 5/1972 | Miller . | |
| 3,806,086 | 4/1974 | Cloyd . | |
| 3,831,629 | 8/1974 | Mackal et al. . | |
| 3,834,380 | 9/1974 | Boyd . | |
| 3,837,381 | 9/1974 | Arroyo . | |
| 3,844,585 | 10/1974 | Sands et al. . | |
| 3,852,385 | 12/1974 | Huggins . | |
| 3,853,127 | 12/1974 | Spademan . | |
| 3,856,010 | 12/1974 | Moorehead et al. . | |
| 3,856,020 | 12/1974 | Kovac . | |
| 3,875,938 | 4/1975 | Mellor . | |
| 3,889,675 | 6/1975 | Stewart . | |
| 3,898,988 | 8/1975 | Morgan | 128/214 R |
| 3,968,508 | 7/1976 | Ikeuchi | 351/209 |
| 3,974,832 | 8/1976 | Kruck | 128/221 |
| 3,976,063 | 8/1976 | Hennemann et al. | 128/142.7 |
| 3,977,400 | 8/1976 | Moorehead | 128/214.4 |
| 3,977,403 | 8/1976 | Patel | 128/221 |
| 3,986,508 | 10/1976 | Barrington | 128/214.2 |
| 3,994,293 | 11/1976 | Ferro | 128/214 R |
| 3,994,516 | 11/1976 | Fredd | 285/39 |
| 4,000,739 | 1/1977 | Stevens | 128/214.4 |
| 4,006,744 | 2/1977 | Steer | 128/214 R |
| 4,019,512 | 4/1977 | Tenczar | 128/214 R |
| 4,040,421 | 8/1977 | Young | 128/218 N |
| 4,063,555 | 12/1977 | Ulinder | 128/214 R |
| 4,076,285 | 2/1978 | Martinez | 285/332 |
| 4,080,964 | 3/1978 | Phillips | 128/214 D |
| 4,084,606 | 4/1978 | Mittleman | 604/256 |
| 4,105,187 | 8/1978 | Huber | 251/334 |
| 4,105,500 | 8/1978 | Libman et al. | 195/103.5 M |
| 4,106,491 | 8/1978 | Guerra | 182/2 F |
| 4,121,585 | 10/1978 | Becker, Jr. | 128/214 |
| 4,128,098 | 12/1978 | Bloom et al. | 128/272.3 |
| 4,133,312 | 1/1979 | Burd | 128/214 R |
| 4,143,853 | 3/1979 | Abramson | 251/149.1 |
| 4,143,858 | 3/1979 | Schmidt, III et al. | 526/48.2 |
| 4,149,535 | 4/1979 | Volder | 128/214.4 |
| 4,161,949 | 7/1979 | Thanawalla | 128/247 |
| 4,177,809 | 12/1979 | Moorehead | 128/214.4 |
| 4,177,814 | 12/1979 | Knepshield et al. | 128/348 |
| 4,187,846 | 2/1980 | Lolachi et al. | 128/214 R |
| 4,192,304 | 3/1980 | Millet | 128/214.4 |
| 4,197,848 | 4/1980 | Garrett et al. | 128/247 |
| 4,200,096 | 4/1980 | Charvin | 128/214.4 |
| 4,201,208 | 5/1980 | Cambio, Jr. | 128/214.2 |
| 4,219,021 | 8/1980 | Fink | 128/214 B |
| 4,219,912 | 9/1980 | Adams | 128/214 G |
| 4,240,411 | 12/1980 | Hosono | 128/4 |
| 4,252,122 | 2/1981 | Halvorsen | 128/349 R |
| 4,266,815 | 5/1981 | Cross | 285/330 |
| 4,294,250 | 10/1981 | Dennehey | 128/247 |
| 4,324,239 | 4/1982 | Gordon et al. | 128/214 R |
| 4,326,569 | 4/1982 | Vaillancourt | 141/383 |
| 4,328,802 | 5/1982 | Curley et al. | 128/272.1 |
| 4,332,333 | 6/1982 | Linsey | 222/83 |
| 4,334,551 | 6/1982 | Pfister | 137/614.03 |
| 4,338,933 | 7/1982 | Bayard et al. | 128/214 R |
| 4,341,224 | 7/1982 | Stevens | 128/675 |
| 4,341,239 | 7/1982 | Atkinson | 137/493 |
| 4,360,024 | 11/1982 | Wallace | 604/256 |
| 4,387,879 | 6/1983 | Tauschinski | 251/149.1 |
| 4,392,856 | 7/1983 | Lichtenstein | 604/177 |
| 4,411,662 | 10/1983 | Pearson | 604/411 |
| 4,421,123 | 12/1983 | Percarpio | 128/766 |
| 4,421,296 | 12/1983 | Stephens | 251/149.7 |
| 4,425,919 | 1/1984 | Alston, Jr. et al. | 128/658 |
| 4,429,856 | 2/1984 | Jackson | 251/149.1 |
| 4,432,755 | 2/1984 | Pearson | 604/56 |
| 4,432,759 | 2/1984 | Gross et al. | 604/411 |
| 4,432,765 | 2/1984 | Oscarsson | 604/411 |
| 4,436,125 | 3/1984 | Blenkush | 141/330 |
| 4,436,519 | 3/1984 | O'Neill | 604/175 |
| 4,439,193 | 3/1984 | Larkin | 604/411 |
| 4,443,219 | 4/1984 | Meisch et al. | 604/317 |
| 4,445,893 | 5/1984 | Bodicky | 604/165 |
| 4,449,693 | 5/1984 | Gereg | 251/149.8 |
| 4,457,749 | 7/1984 | Bellotti et al. | 604/29 |
| 4,457,753 | 7/1984 | Pastrone | 604/153 |
| 4,475,548 | 10/1984 | Muto | 128/207 |
| 4,496,348 | 1/1985 | Genese et al. | 604/167 |
| 4,508,367 | 4/1985 | Oreopoulos et al. | 285/3 |
| 4,511,359 | 4/1985 | Vaillancourt | 604/411 |
| 4,512,766 | 4/1985 | Vailancourt | 604/169 |
| 4,526,572 | 7/1985 | Donnan et al. | 604/29 |
| 4,534,758 | 8/1985 | Akers et al. | 604/85 |
| 4,535,818 | 8/1985 | Duncan et al. | 137/846 |
| 4,535,819 | 8/1985 | Atkinson et al. | 137/846 |
| 4,535,820 | 8/1985 | Raines | 137/854 |
| 4,547,193 | 10/1985 | Rydell | 604/282 |
| 4,566,493 | 1/1986 | Edwards et al. | 137/846 |
| 4,568,081 | 2/1986 | Martin | 273/65 C |
| 4,568,336 | 2/1986 | Cooper | 604/240 |
| 4,573,993 | 3/1986 | Hoag et al. | 604/411 |
| 4,592,356 | 6/1986 | Gutierrez | 128/339 |
| 4,601,703 | 7/1986 | Herlitze | 604/86 |
| 4,607,671 | 8/1986 | Aalto et al. | 141/329 |
| 4,610,276 | 9/1986 | Paradis et al. | 137/856 |
| 4,610,469 | 9/1986 | Wolff-Mooij | 285/260 |
| 4,610,665 | 9/1986 | Matsumoto et al. | 604/167 |
| 4,610,674 | 9/1986 | Suzuki et al. | 604/282 |
| 4,612,960 | 9/1986 | Edwards et al. | 137/846 |
| 4,615,693 | 10/1986 | Paradis et al. | 604/122 |
| 4,617,012 | 10/1986 | Vailancourt | 604/29 |
| 4,623,068 | 11/1986 | Brown et al. | 215/11 R |
| 4,629,159 | 12/1986 | Wellenstam | 251/149.6 |
| 4,629,450 | 12/1986 | Suzuki et al. | 604/164 |
| 4,645,494 | 2/1987 | Lee et al. | 604/175 |
| 4,649,904 | 3/1987 | Krauter et al. | 128/6 |
| 4,655,752 | 4/1987 | Honkanen et al. | 604/256 |
| 4,673,393 | 6/1987 | Suzuki et al. | 604/167 |
| 4,673,394 | 6/1987 | Fenton, Jr. et al. | 604/175 |
| 4,673,400 | 6/1987 | Martin | 604/283 |
| 4,683,916 | 8/1987 | Raines | 137/854 |
| 4,706,487 | 11/1987 | Bandou et al. | 72/355 |
| 4,725,267 | 2/1988 | Vaillancourt | 604/192 |
| 4,728,075 | 3/1988 | Paradis | 251/122 |
| 4,745,950 | 5/1988 | Mathieu | 137/798 |
| 4,752,287 | 6/1988 | Kurtz et al. | 604/99 |
| 4,752,292 | 6/1988 | Lopez et al. | 604/244 |
| 4,758,225 | 7/1988 | Cox et al. | 604/126 |
| 4,759,756 | 7/1988 | Forman et al. | 604/413 |
| 4,765,588 | 8/1988 | Atkinson | 251/149.1 |
| 4,768,568 | 9/1988 | Fournier et al. | 141/286 |
| 4,775,369 | 10/1988 | Schwartz | 604/263 |

| | | | | | | | |
|---|---|---|---|---|---|---|---|
| 4,781,702 | 11/1988 | Herrli | 604/244 | 5,085,645 | 2/1992 | Purdy et al. | 604/167 |
| 4,786,281 | 11/1988 | Valentini et al. | 604/256 | 5,088,984 | 2/1992 | Fields | 604/167 |
| 4,809,679 | 3/1989 | Shimonaka et al. | 128/4 | 5,092,840 | 3/1992 | Healy | 604/83 |
| 4,810,241 | 3/1989 | Rogers | 604/28 | 5,092,857 | 3/1992 | Fleischhacker | 604/256 |
| 4,823,833 | 4/1989 | Hogan et al. | 137/567 | 5,098,405 | 3/1992 | Peterson et al. | 604/247 |
| 4,827,973 | 5/1989 | Boehmer | 137/512.15 | 5,099,878 | 3/1992 | Boehmer | 137/533.29 |
| 4,832,214 | 5/1989 | Schrader et al. | 215/11.1 | 5,100,394 | 3/1992 | Dudar et al. | 604/263 |
| 4,834,152 | 5/1989 | Howson et al. | 141/286 | 5,103,854 | 4/1992 | Bailey | 137/102 |
| 4,834,664 | 5/1989 | Lin | 439/145 | 5,104,379 | 4/1992 | Nakamura et al. | 604/111 |
| 4,834,719 | 5/1989 | Arenas | 604/243 | 5,104,389 | 4/1992 | Deem et al. | 604/264 |
| 4,838,855 | 6/1989 | Lynn | 604/49 | 5,108,380 | 4/1992 | Herlitze et al. | 604/283 |
| 4,838,873 | 6/1989 | Landskron et al. | 604/283 | 5,114,408 | 5/1992 | Fleischhaker et al. | 604/167 |
| 4,842,591 | 6/1989 | Luther | 604/283 | 5,122,123 | 6/1992 | Vaillancourt | 604/192 |
| 4,846,809 | 7/1989 | Sims | 604/198 | 5,127,904 | 7/1992 | Loo et al. | 604/83 |
| 4,850,975 | 7/1989 | Furukawa | 604/170 | 5,129,426 | 7/1992 | Boehmer | 137/854 |
| 4,856,533 | 8/1989 | Anraku et al. | 128/763 | 5,134,489 | 7/1992 | Sauer | 358/213.26 |
| 4,857,062 | 8/1989 | Russell | 604/256 | 5,135,489 | 8/1992 | Jepson et al. | 604/48 |
| 4,863,201 | 9/1989 | Carstens | 285/317 | 5,137,527 | 8/1992 | Miller et al. | 604/415 |
| 4,865,583 | 9/1989 | Tu | 604/53 | 5,139,483 | 8/1992 | Ryan | 604/86 |
| 4,871,356 | 10/1989 | Haindl et al. | 604/247 | 5,147,333 | 9/1992 | Raines | 604/249 |
| 4,874,377 | 10/1989 | Newgard et al. | 604/167 | 5,154,703 | 10/1992 | Bonaldo | 604/244 |
| 4,878,897 | 11/1989 | Katzin | 604/86 | 5,158,554 | 10/1992 | Jepson et al. | 604/283 |
| 4,886,507 | 12/1989 | Patton et al. | 604/284 | 5,163,922 | 11/1992 | McElveen, Jr. et al. | 604/249 |
| 4,895,346 | 1/1990 | Steigerwald | 251/149.1 | 5,167,637 | 12/1992 | Okada et al. | 604/167 |
| 4,908,018 | 3/1990 | Thomsen | 604/83 | 5,167,642 | 12/1992 | Fowles | 604/263 |
| 4,909,798 | 3/1990 | Fleischhacker et al. | 604/256 | 5,167,648 | 12/1992 | Jepson et al. | 604/283 |
| 4,915,687 | 4/1990 | Sivert | 604/83 | 5,171,234 | 12/1992 | Jepson et al. | 604/283 |
| 4,917,668 | 4/1990 | Haindl | 604/167 | 5,178,607 | 1/1993 | Lynn et al. | 604/86 |
| 4,928,212 | 5/1990 | Benavides | 362/61 | 5,179,174 | 1/1993 | Elton | 525/409 |
| 4,935,010 | 6/1990 | Cox et al. | 604/122 | 5,184,652 | 2/1993 | Fan | 141/21 |
| 4,943,896 | 7/1990 | Johnson | 362/84 | 5,188,620 | 2/1993 | Jepson et al. | 141/21 |
| 4,944,732 | 7/1990 | Russo | 604/247 | 5,190,067 | 3/1993 | Paradis et al. | 137/1 |
| 4,946,904 | 8/1990 | Krauter et al. | 604/167 | 5,195,980 | 3/1993 | Catlin | 604/167 |
| 4,950,257 | 8/1990 | Hibbs et al. | 604/265 | 5,199,948 | 4/1993 | McPhee | 604/86 |
| 4,950,260 | 8/1990 | Bonaldo | 604/263 | 5,201,725 | 4/1993 | Kling | 604/284 |
| 4,954,149 | 9/1990 | Fullemann | 55/386 | 5,203,775 | 4/1993 | Frank et al. | 604/256 |
| 4,961,412 | 10/1990 | Fink | 604/167 | 5,207,656 | 5/1993 | Kranys | 604/256 |
| 4,964,855 | 10/1990 | Todd et al. | 604/283 | 5,211,634 | 5/1993 | Vaillancourt | 604/256 |
| 4,966,588 | 10/1990 | Raymann et al. | 604/165 | 5,211,638 | 5/1993 | Dudar et al. | 604/283 |
| 4,969,879 | 11/1990 | Lichte | 604/283 | 5,215,537 | 6/1993 | Lynn et al. | 604/244 |
| 4,969,883 | 11/1990 | Gilbert et al. | 604/414 | 5,215,538 | 6/1993 | Larkin | 604/249 |
| 4,981,469 | 1/1991 | Whitehouse et al. | 604/86 | 5,230,706 | 7/1993 | Duquette | 604/83 |
| 4,984,829 | 1/1991 | Saigo et al. | 285/334 | 5,234,410 | 8/1993 | Graham et al. | 604/167 |
| 4,986,310 | 1/1991 | Bailey et al. | 137/859 | 5,242,393 | 9/1993 | Brimhall et al. | 604/86 |
| 4,998,713 | 3/1991 | Vaillancourt | 604/283 | 5,242,423 | 9/1993 | Goodsir et al. | 604/243 |
| 4,998,921 | 3/1991 | Vickroy et al. | 604/167 | 5,242,432 | 9/1993 | DeFrank | 604/284 |
| 4,998,927 | 3/1991 | Vaillancourt | 604/283 | 5,249,598 | 10/1993 | Schmidt | 137/493.1 |
| 5,000,745 | 3/1991 | Guest et al. | 604/256 | 5,250,033 | 10/1993 | Evans et al. | 604/160 |
| 5,006,114 | 4/1991 | Rogers et al. | 604/167 | 5,251,873 | 10/1993 | Atkinson et al. | 251/149.1 |
| 5,006,118 | 4/1991 | Yule | 604/408 | 5,256,155 | 10/1993 | Yerlikaya et al. | 604/246 |
| 5,009,391 | 4/1991 | Steigerwald | 251/149.1 | 5,261,459 | 11/1993 | Atkinson et al. | 137/846 |
| 5,009,490 | 4/1991 | Kouno et al. | 350/342 | 5,269,763 | 12/1993 | Boehmer et al. | 604/167 |
| 5,010,925 | 4/1991 | Atkinson et al. | 137/847 | 5,269,771 | 12/1993 | Thomas et al. | 604/213 |
| 5,018,532 | 5/1991 | Etheredge, III | 128/844 | 5,273,533 | 12/1993 | Bonaldo | 604/83 |
| 5,041,087 | 8/1991 | Loo et al. | 604/83 | 5,279,571 | 1/1994 | Larkin | 604/167 |
| 5,041,095 | 8/1991 | Littrell | 604/167 | 5,280,876 | 1/1994 | Atkins | 251/149.1 |
| 5,041,097 | 8/1991 | Johnson | 604/167 | 5,289,849 | 3/1994 | Paradis | 137/606 |
| 5,046,456 | 9/1991 | Heymann et al. | 119/106 | 5,290,254 | 3/1994 | Vaillancourt | 604/192 |
| 5,049,128 | 9/1991 | Duquette | 604/83 | 5,295,657 | 3/1994 | Atkinson | 251/149.1 |
| 5,057,092 | 10/1991 | Webster, Jr. | 604/282 | 5,295,658 | 3/1994 | Atkinson et al. | 251/149.1 |
| 5,059,186 | 10/1991 | Yamamoto et al. | 604/280 | 5,296,771 | 3/1994 | Sakuma et al. | 310/220 |
| 5,060,812 | 10/1991 | Ogle, II | 215/247 | 5,301,707 | 4/1994 | Hofsteenge | 137/12 |
| 5,061,253 | 10/1991 | Yoshida | 604/246 | 5,306,243 | 4/1994 | Bonaldo | 604/86 |
| 5,061,738 | 10/1991 | Solomon et al. | 523/100 | 5,312,362 | 5/1994 | Pfolsgraf et al. | 604/167 |
| 5,064,416 | 11/1991 | Newgard et al. | 604/167 | 5,312,377 | 5/1994 | Dalton | 604/283 |
| 5,065,783 | 11/1991 | Olge, II | 137/68.1 | 5,330,435 | 7/1994 | Vaillancourt | 604/167 |
| 5,069,225 | 12/1991 | Okamura | 128/765 | 5,330,437 | 7/1994 | Durman | 604/167 |
| 5,069,424 | 12/1991 | Dennany, jr. et al. | 251/149.6 | 5,336,192 | 8/1994 | Palestrant | 604/167 |
| 5,070,905 | 12/1991 | Paradis | 137/606 | 5,344,414 | 9/1994 | Lopez et al. | 604/283 |
| 5,071,404 | 12/1991 | Larkin et al. | 604/86 | 5,349,984 | 9/1994 | Weinheimer et al. | 137/543.21 |
| 5,078,699 | 1/1992 | Haber et al. | 604/250 | 5,353,837 | 10/1994 | Faust | 137/614.18 |
| 5,080,654 | 1/1992 | Picha et al. | 604/167 | 5,360,413 | 11/1994 | Leason et al. | 604/249 |

| | | | | | | |
|---|---|---|---|---|---|---|
| 5,368,801 | 11/1994 | Vaillancourt ........................ 264/249 | | 5,695,466 | 12/1997 | Lopez et al. ........................ 604/93 |
| 5,370,636 | 12/1994 | Von Witzleben ..................... 604/83 | | 5,699,821 | 12/1997 | Paradis . |
| 5,380,306 | 1/1995 | Brinon ................................ 604/244 | | 5,700,248 | 12/1997 | Lopez ................................ 604/249 |
| 5,390,898 | 2/1995 | Smedley et al. ................... 251/149.6 | | 5,702,019 | 12/1997 | Grimard ............................. 215/301 |
| 5,395,348 | 3/1995 | Ryan .................................. 604/247 | | 5,727,770 | 3/1998 | Dennis ............................... 604/256 |
| 5,401,245 | 3/1995 | Haining .............................. 604/86 | | 5,738,663 | 4/1998 | Lopez ................................ 604/249 |
| 5,402,982 | 4/1995 | Atkinson et al. .................. 251/149.1 | | 5,749,861 | 5/1998 | Guala et al. . |
| 5,409,125 | 4/1995 | Kimber et al. ...................... 215/32 | | 5,776,113 | 7/1998 | Daugherty et al. . |
| 5,409,471 | 4/1995 | Atkinson et al. ................... 604/289 | | 5,788,675 | 8/1998 | Mayer . |
| 5,417,672 | 5/1995 | Nita et al. ........................... 604/283 | | 5,820,601 | 10/1998 | Mayer . |
| 5,417,673 | 5/1995 | Gordon ............................... 604/283 | | 5,836,923 | 11/1998 | Mayer . |
| 5,437,646 | 8/1995 | Hunt et al. .......................... 604/167 | | B1 5,251,873 | 5/1995 | Atkinson et al. ................. 251/149.1 |
| 5,439,451 | 8/1995 | Collinson et al. .................. 604/247 | | | | |
| 5,441,486 | 8/1995 | Yoon .................................. 604/167 | | | FOREIGN PATENT DOCUMENTS | |
| 5,441,487 | 8/1995 | Vedder ............................... 604/167 | | | | |
| 5,445,630 | 8/1995 | Richmond .......................... 604/414 | | 0237321 | 9/1987 | European Pat. Off. . |
| 5,453,097 | 9/1995 | Paradis .............................. 604/247 | | 0 240 987 | 10/1987 | European Pat. Off. . |
| 5,456,284 | 10/1995 | Ryan et al. ......................... 604/159 | | 0 309 771 | 4/1989 | European Pat. Off. . |
| 5,456,675 | 10/1995 | Wolbring et al. ................... 604/280 | | 0 309 771 | 5/1989 | European Pat. Off. . |
| 5,458,640 | 10/1995 | Gerrone ............................. 604/264 | | 0 343 953 A1 | 11/1989 | European Pat. Off. . |
| 5,462,255 | 10/1995 | Rosen et al. ...................... 251/149.6 | | 0399119 | 11/1990 | European Pat. Off. . |
| 5,465,938 | 11/1995 | Werge et al. ...................... 251/149.1 | | 0 414 997 A1 | 3/1991 | European Pat. Off. . |
| 5,466,219 | 11/1995 | Lynn et al. .......................... 604/86 | | 0446463A1 | 9/1991 | European Pat. Off. . |
| 5,471,319 | 11/1995 | Mayer ................................ 604/167 | | 0 696 460 A2 | 2/1996 | European Pat. Off. . |
| 5,474,536 | 12/1995 | Bonaldo ............................. 604/86 | | 0 696 461 A2 | 2/1996 | European Pat. Off. . |
| 5,474,541 | 12/1995 | Ritsky et al. ....................... 604/213 | | 0 798 013 A1 | 1/1997 | European Pat. Off. . |
| 5,474,544 | 12/1995 | Lynn .................................. 604/283 | | 0 811 560 A2 | 12/1997 | European Pat. Off. . |
| 5,487,728 | 1/1996 | Vaillancourt. ...................... 604/86 | | 1149727 | 12/1957 | France . |
| 5,487,731 | 1/1996 | Denton ............................... 604/100 | | 2049513 | 3/1971 | France . |
| 5,492,147 | 2/1996 | Challender et al. ............. 137/614.05 | | 2 337 670 | 1/1976 | France . |
| 5,492,304 | 2/1996 | Smith et al. ....................... 251/149.1 | | 2907-832 | 9/1980 | Germany . |
| 5,501,426 | 3/1996 | Atkinson et al. .................. 251/149.1 | | 30 31 242 A1 | 3/1982 | Germany . |
| 5,509,433 | 4/1996 | Paradis .............................. 137/1 | | 30 42 229 A1 | 5/1982 | Germany . |
| 5,509,912 | 4/1996 | Vaillancourt et al. .............. 604/283 | | 32 42 870 A1 | 6/1983 | Germany . |
| 5,514,098 | 5/1996 | Pfoslgraf et al. .................. 604/167 | | 33 03 718 C1 | 10/1984 | Germany . |
| 5,514,116 | 5/1996 | Vaillancourt et al. .............. 604/283 | | A 61 | 10/1985 | Germany . |
| 5,520,665 | 5/1996 | Fleetwood . | | 37 37 665 A1 | 11/1987 | Germany . |
| 5,529,278 | 6/1996 | Weldon et al. ..................... 251/4 | | 38 09 127 | 3/1988 | Germany . |
| 5,531,810 | 7/1996 | Fullemann ......................... 96/105 | | 1634-936 | 3/1991 | Russian Federation . |
| 5,533,708 | 7/1996 | Atkinson et al. .................. 251/149.1 | | 1708050 | 11/1967 | United Kingdom . |
| 5,533,983 | 7/1996 | Haining .............................. 604/249 | | 2 012 919 | 8/1979 | United Kingdom . |
| 5,535,771 | 7/1996 | Purdy et al. ........................ 137/15 | | WO 86/01712 | 3/1986 | WIPO . |
| 5,535,785 | 7/1996 | Werge et al. ...................... 137/843 | | WO 86/03416 | 6/1986 | WIPO . |
| 5,540,661 | 7/1996 | Tomisaka et al. ................. 604/265 | | WO 88/01881 | 3/1988 | WIPO . |
| 5,549,566 | 8/1996 | Elias et al. ......................... 604/167 | | WO 89/06553 | 7/1989 | WIPO . |
| 5,549,577 | 8/1996 | Siegel et al. ....................... 604/256 | | WO 90/11103 | 10/1990 | WIPO . |
| 5,549,651 | 8/1996 | Lynn .................................. 604/283 | | WO/91/06255 | 5/1991 | WIPO . |
| 5,552,118 | 9/1996 | Mayer ................................ 422/103 | | WO 92/04936 | 4/1992 | WIPO . |
| 5,555,908 | 9/1996 | Edwards et al. .................. 137/329.1 | | PCT/US91/ | | |
| 5,556,388 | 9/1996 | Johlin, Jr. .......................... 604/263 | | 06604 | 6/1992 | WIPO . |
| 5,569,235 | 10/1996 | Ross et al. ......................... 604/403 | | WO 93/11828 | 6/1993 | WIPO . |
| 5,573,516 | 11/1996 | Tyer ................................... 604/249 | | WO/93/11828 | 6/1993 | WIPO . |
| 5,578,059 | 11/1996 | Patzer ................................ 604/249 | | WO 95/15194 | 6/1995 | WIPO . |
| 5,584,808 | 12/1996 | Healy ................................. 604/103 | | WO 96/00053 | 1/1996 | WIPO . |
| 5,597,536 | 1/1997 | Mayer ................................ 422/103 | | WO 96/40359 | 12/1996 | WIPO . |
| 5,616,130 | 4/1997 | Mayer ................................ 604/167 | | WO 97/00702 | 1/1997 | WIPO . |
| 5,620,434 | 4/1997 | Brony et al. ....................... 604/406 | | WO 97/21463 | 6/1997 | WIPO . |
| 5,674,206 | 10/1997 | Allton et al. ........................ 604/249 | | WO 97/24548 | 7/1997 | WIPO . |
| 5,676,130 | 10/1997 | Mayer ................................ 604/167 | | WO 97/38744 | 10/1997 | WIPO . |
| 5,685,866 | 11/1997 | Lopez ................................ 604/249 | | WO 98/17192 | 1/1998 | WIPO . |
| 5,688,254 | 11/1997 | Lopez et al. ....................... 604/93 | | WO98/50106 | 4/1998 | WIPO . |
| 5,690,612 | 11/1997 | Lopez et al. ....................... 604/93 | | WO 98/23313 | 6/1998 | WIPO . |
| 5,694,686 | 12/1997 | Lopez ................................ 29/890.126 | | WO 98/26835 | 6/1998 | WIPO . |

NEEDLELESS CONNECTOR

This application claims the benefit of U.S. Provisional Application No. 60/047,161, filed May 20, 1997.

FIELD OF THE INVENTION

The present invention relates generally to needleless fluid connection devices and more specifically to a device for repeatedly establishing a sealed connection to a conduit or a container for medical applications.

BACKGROUND OF THE INVENTION

One very prevalent form of health care therapy is infusion or intravenous ("I.V.") therapy whereby fluids possessing desired medication or other characteristics are infused into a patient over varying lengths of time. To practice this infusion therapy frequently a connection needs to be made between components for the transfer of fluid between the two components, along a fluid passageway and eventually to a patient. As an example, administration sets are widely used to administer liquids parenterally to a patient and other medical devices are connected to the administration set to provide the proper administration.

One widely used connector for making a connection between medical devices to establish a fluid passageway is a luer connection assembly. In the luer connection assembly, a male luer tip component or fitting having a frustoconical shape is inserted into a female luer component or fitting having a frustoconical shaped receiving cavity and opposing conical surfaces come into contact to form a sealed friction fit.

Until the connection is made, the passageway through each of the luer fittings and into the lumen of a component attached to the luer fitting is open to the environment. This lumen and the passageway through the luer connectors form a portion of the fluid passageway and must be sterile prior to use and then sealed against microbial ingress during use. Thus, these connection assemblies and the associated components are packaged in sterile packaging and the connections are typically made just prior to establishing fluid communication with a patient's venous system.

There are two general types of luer connection assemblies. One type is generally referred to as the luer slip where the connection is maintained by the friction fit between the male luer tip and female luer component. The other type is generally referred to as a luer lock connection whereby the male luer tip is encircled by an annular flange having a threaded internal surface. The female component includes a corresponding thread formed about the outer surface. Engaging the threaded flange to the threaded outside surface establishes the connection between the male luer tip and female component while preventing accidental disconnects.

To insure a universal luer connections among components provided by a multitude of manufacturers, luer connection assemblies are manufactured to comply with universal standards. Very important sets of standards such as ANSI and ISO standards. These standards includes standard dimensions for male slip and luer lock assemblies. Among these dimensional standards are standards which define the spacing or clearance between the annular locking flange and the male luer tip. Thus any female connection device configured to establish a connection to a standard male luer lock must be able to engage the luer tip and locking flange within this clearance or spacing.

Other standards in the ISO standards include several performance requirements for luer connections. One such requirement is that after a luer lock type connection is made, to prevent inadvertent disconnection, the luer connection should resist an axial removal force of 8 pounds and unscrewing torque less than 2.8 in/oz without disconnection. Luer connections should also hold a seal against 45 psi after a connection torque of 16 in/oz has been applied. In standard luer connections this resistance and sealing is supplied by the friction between the opposing conical surfaces.

Once a component of I.V. therapy is placed in fluid communication with the body, the fluid passageway should be sealed from the environment to prevent contamination and this passageway should also be sealed so as to not allow any leakage of bodily fluids into the environment. However, most therapies require periodic access to the fluid passageway. Because the portion of the fluid passageway through a female luer connection component is open to the environment, these components will not form a sealed connection to the fluid passageway after the fluid passageway is placed in fluid communication with the body.

In one prevalent example of intravenous therapy, fluid containing a drug in solution is injected into a primary flow of fluid from an I.V. solution container through an administration set to a catheter extending within a vein. The drug containing fluid may be injected from a syringe, secondary medication set or the like, into the set where it mixes with the flowing fluid. In another prevalent example, fluid is injected directly into or withdrawn from a catheter extending within the body. In addition the catheters are flushed periodically to maintain patency by the injection of small amounts of saline or heparin.

As can be appreciated, it is highly desirable to maintain catheters and administration sets in service as long as possible without compromising the safety of the patient. Replacement of catheters and sets is time consuming and expensive. Therefore over the period of time of use of a set or catheter there may be many connections and disconnects. For example, there may be over 100 connections and disconnects to a connection site on a catheter or set before the catheter or set is replaced. In addition a connection may be made and that connection maintained for an extended period of time before disconnection. For example a connection may be made for up to seven days of "indwell" and yet the connection should still be capable of accepting intermediate and subsequent connections and disconnects without allowing leakage to the environment.

Another highly desirable attribute of a connector is the ability for such a connector to seal against pressurized fluid found within a set or for the connector to possess a certain leak pressure in excess of a desired pressure. For example it is desirable for a connector to have a leak pressure which is in excess of 20 p.s.i. for a short period of time such as when a bolus administration of drug is injected into a set and a leak pressure in excess of 6 p.s.i. of continuous pressure during infusion of medication.

In addition, a connector may be exposed to negative pressure particularly when such connector is located upstream of an inlet of an intravenous pump. Failure to prevent aspiration through a connector when the connector is exposed to negative pressure may lead to an aspiration of air and/or microbes into the fluid passageway.

Depending on the application, many other features may be desirable. Dead spaces within any connector which cannot be "flushed" should be minimized or eliminated as they may form an environment for microbial growth. Also, priming volume for the connector should be minimized.

Because intravenous therapy is practiced on a worldwide basis and millions of connection sites are used every year and the costs of components used in such therapy are a factor in the cost of therapy, any desired connector should be capable of being manufactured at high speeds and low cost. Generally the lower the number of parts making up a component, the lower the number of molds and high speed assembly devices both of which generally translate to lower capital expenditures and therefore lower costs.

On the other hand, whatever the connector configuration, it is highly desirable that the connector be capable of low defect manufacture. Even a small number of failure is generally unacceptable when a single failure may put a patient or health care provider at risk.

Moreover, it is also highly desirable that any surfaces around an inlet into a connector be able to be swabbed or otherwise disinfected. Typically unbroken or smooth surfaces facilitate swabbing and other disinfecting techniques.

As mentioned previously, although luer connectors are widely found in the medical environment such connections are generally not acceptable when many of the above described requirements need to be satisfied. This is primarily due to the fact that the opening through the luer connector is not sealed so that upon disconnection the opening and the fluid passageway are open to the environment which would pose a health hazard to the patient.

Another factor which prevents use of luer connection assemblies in administration sets or injection sites is the inability for such a connector to seal against the pressurized fluid found within a set unless that connector is sealed or connected to a mating connector. The opening in a luer fitting will obviously allow such a pressurized fluid to leak.

To allow the sealed connections and disconnects to a fluid passageway extending in a set or catheter, on many sets there are one or more injection sites having a solid resilient septum in a housing are placed on the set or catheter. A sharpened needle is used to penetrate the septum to provide a connection to the fluid passageway. Although such connections possess many of the desired characteristics for sealed connections, the sharpened needles poses a needlestick hazard.

To combat the needlestick hazard, one embodiment of a needleless systems has been developed which utilizes a resealable septum formed with a slit and compressed within a housing. These needleless systems performed quite well; however, the septum can not be penetrated with a male luer tip and thus a blunt cannula is utilized having a diameter smaller than a male luer tip. If the device to which a connection needs to be made has a luer connector, these blunt cannula are generally attached to the luer fitting. The requirement of the blunt cannula potentially increases the costs of using these types of connectors.

Another type of needleless systems use connectors which are constructed to establish a connection directly with the male luer tip whether such luer tip forms a part of a luer slip or a luer lock. However connections which are to be established with a male luer tip in a manner similar to a luer lock connection described above must be capable of fitting within the standard spacing between a luer tip and locking flange and should also meet other standards which have been set out for such connections.

Examples of these systems' connectors to establish a connection directly with a male luer tip are shown in U.S. Pat. No. 5,685,866, the disclosure of which is incorporated by reference herein. These connectors appear to all possess shortcomings which hinder widespread acceptance by medical practitioners. In general, all of these devices perform in an inferior manner when measured relative to the desirable qualities for connector devices discussed above and also in comparison to the performance standards of a injection site for a sharpened needle and resilient septum or a blunt cannula and pre-slit resilient septum.

For example, several connectors utilize a resilient boot or other seal which is placed within a housing and collapsed by the introduction of a male luer tip. Upon removal of the tip, such collapsing boots must then recover to reseal the connection. Many or these boots stick in the collapsed position which leads to leaking. In addition these moving parts present an interface between the movable boot and housing into which fluid may flow and collect and such collected fluids form a fertile environment for microbial growth, and recessed surfaces and gaps are hard to disinfect. Moreover, the spikes act as flow restrictors and may impart severe turbulence to fluid as it flows through the openings in the spike. Furthermore, after withdrawal of a male luer tip the boots may not recover quickly enough to seal the entrance through the connector and the fluid passageway may be briefly exposed to the environment.

One type of such luer tip connectors has a spike within the housing which penetrates a collapsing boot. The spike has openings proximate an end adjacent the boot and form an internal passageway for the flow of fluid which is opened when the spike penetrates the collapsed boot and spreads the slit. Upon recovery, any slit or opening in the boot must reseal. However, the spike design has exhibited unsatisfactory leakage after a number of connects and disconnects which does not provide for extended use of a set or catheter.

In addition, these connectors have a multitude of parts which increases manufacturing costs and opportunities for malfunction. These designs also produce a connector having voids which cannot be flushed such that stagnant fluid may collect. Moreover, several of these device have potential passageways from voids within the housing but outside the primary fluid passageway, into the primary fluid passageway which may allow any microbial growth within the housing to enter the fluid passageway. Also the interface between the housing and boot is difficult to swab when the boot is in the uncompressed position.

A device described in U.S. Pat. No. 5,616,130, the disclosure of which is incorporated by reference herein, utilizes an elongated cam to spread open a slit in a collapsing boot, and would appear to possess several of the shortcomings of the spike and boot designs described above.

It is generally not a problem for the boot connectors to have ends which engage the male tip and locking flange on a standard luer lock. The sealing mechanism is below the end of the luer tip when the tip is engaged to the connector, thus there is a large amount of flexibility in the configuration of the end of the connector housing which engages the male luer lock.

To overcome many of these deficiencies, needleless connections which utilize a preslit septum as one of the components were developed. These connectors establish a connection with the penetration of the slit in the septum by the luer tip. One such connector is shown and described in U.S. Pat. No. 5,578,059, the disclosure of which is incorporated by reference herein. In the disclosed valve, a resilient preslit septum is utilized to form an environmental barrier. The septum is sealingly captured or held to the housing by having a lower flange which is pinched between a retainer and housing. It appears that the radially extending portion having a slit is maintained in position by the column strength of an outer axially extending cylindrical portion extending upward from the lower flange. However the septum appears not to be capable of sealing against the pressurized fluid found in a set. Thus the valve uses a second lower check type valve to seal against the pressure.

To satisfy ISO dimensional standards and torque removal resistance standards the outer portion of the retainer is formed with a tapered threads so that the connection to a luer lock's straight thread design is similar to a standard NPTF/NPSI connection. The tapered thread design extends over the end of the housing that engages the threads on a male luer lock. Such a thread design may produce too rapid an increase in engaging force during the connection which may lead to a lock up of the luer lock to the connector.

Such a device suffers from several other drawbacks. The valve includes a number of components to make up the housing, the environmental valve and check valve, and this high number of components increases manufacturing costs. In addition, maintaining the septum in position by the column strength of the axially extending portion of the septum forces that portion to have a relatively large thickness. Thus for the septum, the axially extending wall and surrounding housing to fit within the clearance between the luer tip and the locking flange upon penetration of a male luer tip to a desired depth, the housing must be thinned. Such a thinned housing may fracture upon repeated connections and disconnects.

A second connector is described in U.S. Pat. No. 5,533,708, the disclosure of which is incorporated by reference herein. This connector also utilizes a preslit septum which is supported on an axially extending column having sufficient thickness to support the septum upon introduction of the male luer tip. The further provide sufficient column strength the axially extending portion is also formed with a specific tapered shape including a thickened lower portion. To seal the slit during introduction and removal of a luer tip, the underside of the pre-slit radial portion of the septum is formed with biasing ribs.

This connector also uses a retainer which pinches a lower radial flange to sealingly fix the septum to the housing. Thus the connector includes three separate pieces. In addition the thickened axially extending portion of the septum forces the retainer to be thinned such that to presumably supply strength to the retainer the stated preferred material for the retainer is metal which increases manufacturing costs. In addition it is believed that such valves will not exhibit satisfactory leak pressure after long periods of indwell, likely due to compression set of the septum material due to a perceived high level of compression of the septum material between the tip and retainer.

To supply the necessary unscrewing resistance, the retainer is tapered outward proximate the end to establish a frictional engagement with the threads on a male luer lock.

Another feature which is desired by some users, is that a connector not siphon fluid from an attached tubing or catheter into the connector upon removal of the luer tip as this may cause fluid to flow into the other end of the catheter which it is felt may lead to blockage of the tubing. In addition it is desired that a connector is provided which actually expels fluid from the connector upon removal of the luer tip and preferably expels such fluid in a controlled manner.

Therefore, it is a main object of the invention to overcome those disadvantages of the prior art which prevent widespread acceptance of needleless valves which do not require a blunt cannula.

There are other secondary objects, one or more if satisfied may promote market acceptance but satisfaction of each may not be necessary. One object of the present invention is to provide a needleless connector fitting which may be actuated by a male luer tip without using a sharpened needle or an adapter such as a blunt cannula or the like. A related object is to provide a connector which may engage a standard luer lock fitting. A further related object is to provide such a connector which may be coupled to a standard male luer lock and complies as much as possible with ISO and ANSI standards for luer connectors.

Another object of the present invention is to provide a connector which possess sufficient strength to avoid cracking or fracture.

It is a further object of the present invention to provide a connector device which utilizes a minimum number of parts and therefore minimizes opportunity for malfunction.

It is another object of the present invention to provide a connector device which is capable of providing for a large number of connections and disconnects while maintaining the ability to seal against fluids under pressures typically found in an administration set. A related object is to provide such a connector which is capable of providing a minimum of 100 connects and disconnects without compromising the performance.

It is yet a further object of the present invention to provide a connector which upon a disconnection, maintains a leak pressure of 6 psi. constant pressure and 20 psi transient pressure after 4 days of indwell.

It is a further object of the present invention to provide a connector which is capable of high speed manufacturing. It is a related object of the present invention to provide a connector which may be manufactured with a very low number of potential defects.

It is yet another object of the present invention to provide a connector which minimizes voids which cannot be flushed in which stagnant fluid can collect to form a media for microbial growth. It is a related object of the present invention to provide a connector which forms a sealed fluid path such that a minimum number of microbes enter the fluid path during operation using aseptic techniques. It is a further related object to provide a connector which requires a low priming volume.

It is still a further object of the present invention to provide a connector which minimizes or eliminates flow restrictions for the flow of fluid through the connector. In addition it is an object to provide a connector having smooth unbroken surfaces about any inlet to facilitate aseptic techniques.

It is yet another object of the present invention to provide a connector which forms a continuous closed system which seals the fluid passageway from the environment during and after insertion of a male luer tip and instantaneously after withdrawal of the luer tip.

It is a further object of the present invention to provide a connector which does not siphon fluid into the connector from an attached medical device upon removal of a luer tip. A related object is to provide a connector which provides a flow of fluid from the connector during and possibly after removal of the luer tip.

SUMMARY OF THE INVENTION

The above main object is satisfied by connector utilizing a resealable valve having an opening extending through at least a portion of the valve. The valve is resiliently restrained relative to a housing with the valve and housing configured to accept a penetrating member having a tip which penetrates the valve through the opening.

One or more of the secondary objects are satisfied by a valve uniquely configured to seal against pressures typically found in fluid passageways which are in fluid communication with the body. Preferably the resealable valve is a septum and the septum and housing are uniquely configured to accept male luer tips. In one embodiment, the septum includes an upper generally disk shaped upper portion covering an opening defined by the housing and a portion extending downward from the upper portion with the valve opening extending through both the upper and lower portion.

The upper portion of the valve is resiliently retained relative to the housing by integral attachment with an annular skirt and the skirt may be attached to the interior surface of the housing in a first embodiment and surrounding and attached to an exterior surface of the housing in a second embodiment.

DETAILED DESCRIPTION

The following description is not intended to limit the claimed invention to the described embodiments and the disclosed combination of features in the various embodiments might not be absolutely necessary for the inventive solution.

Figure 1:
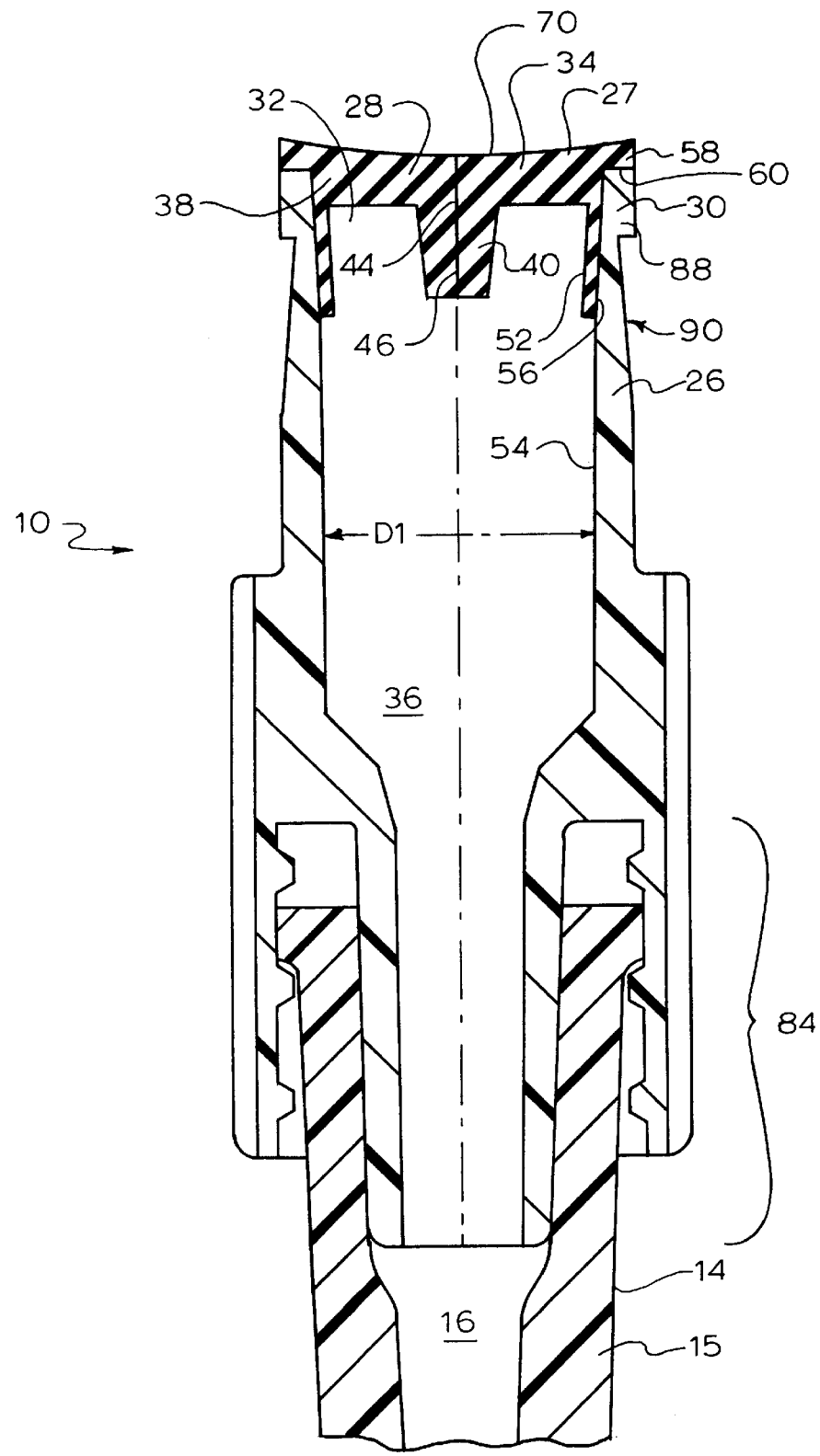
FIG. 1 is a section view of a first embodiment of a needleless connector of the present invention.
Figure 2:
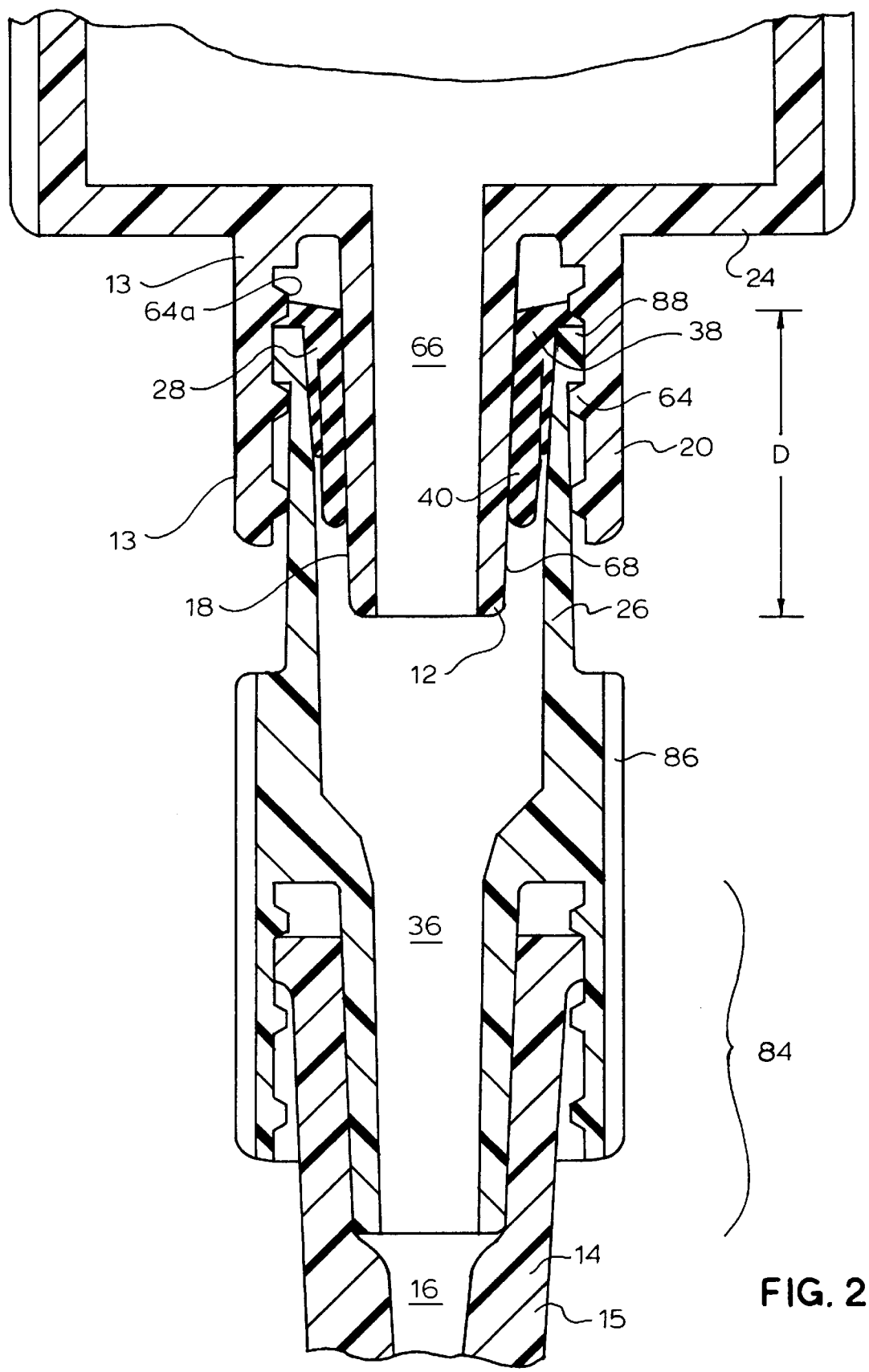
FIG. 2 is a section view of the connector of FIG. 1, shown connected to a male luer tip.

Referring to FIG. 1, a first embodiment of a connector device of the present invention is generally indicated at 10. The connector 10 generally provides multiple fluid connections with a penetrating member 12 (FIG. 2). In an example, the connector 10 may be attached to a conduit 14 in fluid communication with the human body. The conduit 14 may be a peripheral catheter 15, medical tubing or the like and forming a passageway 16 in fluid communication with the body for the flow of fluid to or from a body. The connector 10 may also be attached to other devices such as a vial or vial adapter (not shown) or the like or the connector may be used in lieu of open female luer fittings such as fittings on stopcocks.

Referring to FIG. 2, in an example, the penetrating member 12 is preferably a male luer slip or luer lock 13 conforming to ANSI or ISO standards; however, examples of other members, with appropriate modifications to the housing and septum, may include blunt cannula, needles, specially designed connectors or the like. The luer lock 13 includes a luer tip 18 which, in the embodiment shown, is encircled by a locking flange 20 and forms the end of a syringe 24. Other devices which may utilize a penetrating member 12 include I.V. sets, blood collection and peritoneal dialysis devices and the like.

Referring also to FIG. 1, the connector 10 includes a housing 26 and an elastic and resilient resealable member 27, preferably a septum 28, disposed at an upper end 30 of the housing to seal an opening 32 defined by the upper end 30. The septum 28 is operably connected to the housing 26 with a central portion 34 elastically restrained relative to the housing such that the central portion 34 may be stretched downward into the housing as the penetrating member 12 is inserted into the opening. The central portion 34 elastically retracts upon removal of the penetrating member 12. The housing 26 forms an axially extending passageway 36 which extends downward from the opening 32 and is in fluid communication with the lower passageway 16 defined by the conduit 14. The resealable member 27 is uniquely configured to seal the opening 32 when the central portion 34 is in the occluding position shown in FIG. 1.

The central portion 34 of the septum 28 has a generally disk shaped upper portion 38 and a lower portion 40 extending axially downward within the passageway. A resealable opening 44, such as a slit 46 extends downward preferably through both the upper portion 38 and lower portion 40. It is anticipated that the opening 44 may be formed so that initially the opening may extend only through a portion of one or both of the upper and lower portions 38, 40; however, extending a penetrating member 12 completely through the septum 28 will force the opening to also extend completely through the septum 28. Preferably the opening 44 is configured in such a manner such that when the penetrating member 12 extends completely through the septum 28 the upper and lower portions 38, 40 are elastically stretched about the penetrating member to seal against leakage through the interface between the penetrating member and the septum.

The slit length in the horizontal direction is preferably shorter than one half the circumference of the tip end of the luer tip 18.

Figure 3:
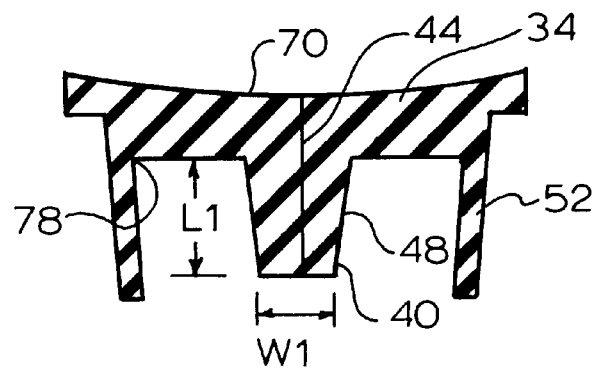
FIG. 3 is a section view of a septum forming a part of the connector of FIG. 1.
Figure 3A:
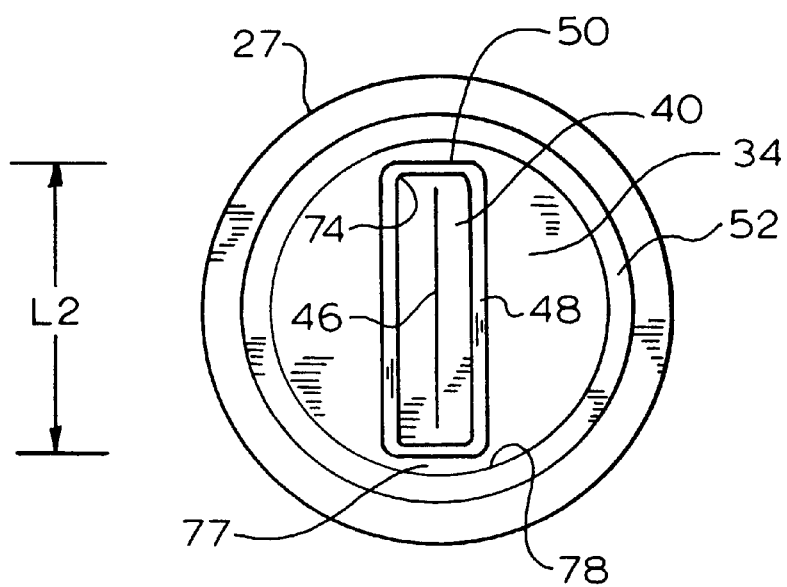
FIG. 3a is a bottom plan view of a septum forming a part of the connector of FIG. 1.

As shown in FIG. 3 and 3a, in the first embodiment, the lower portion 40 forms a generally rectangular horizontal cross section. Vertically extending sidewalls 48 and end walls 50 are slightly tapered so that the lower portion 40 forms a trapezoidal vertical cross section which facilitates molding and orienting the septum during manufacturing particularly when forming an opening 44. The opening 44 may extend straight downward or be oriented at an angle relative to the vertical. In addition, the opening 44 may be a slit 46 or may be curved or slightly helically rotated to promote the sealing of the opening.

Referring back to FIG. 1, the septum 28 includes an annular skirt 52 which extends downward within the passageway 36 and is attached to the inner surface 54 of the housing 26 to elastically restrain the central portion 34 relative to the housing. The attachment is preferably made by adhesively bonding an outer surface 56 of the skirt 52 to the inner surface 54. Because displacement of the central portion 34 into the passageway 36 by the luer tip 18 (FIG. 2) applies shear stress to the attachment between the skirt 52 and housing 26, the septum 28 includes a radial lip 58 which extends over and is attached to an upper edge 60 of the housing. The attachment of the lip 58 and edge 60 at least partially supports the skirt 52 and aids in resisting the shear forces. In the first embodiment, the attachment between the lip 58 and edge 60 is by an adhesive bond in the same manner as the attachment of the housing and the skirt 52.

Referring to FIG. 2, to insure universal connectivity, it is preferable that dimensions of luer connecting devices are standardized to ISO standards. For example, the dimensions of the luer tip 18 including the taper are set by the standard. Similarly threads 64 on the inside of the locking flange 20 define a clearance radius which is set by the standard. As can be appreciated, when the male luer tip 18 extends within the connector 10 and the locking flange 20 extends about the exterior of the connector, the size of the connector and its components are constrained within the spacing between the luer tip and locking flange. Also, according to ISO standards, the male luer tip 18 should be able to penetrate to a desired insertion depth "D" of 0.300 inches which additionally constrains the size of the connector 12 and its components particularly about the upper end 30 of the housing 26 which must fit within the spacing between the luer tip 18 and locking flange 20.

In FIG. 2 the luer tip 18 is shown forcing the septum 28 into an open position. In particular the tip 18 extends through the opening 44 to the desired depth D, establishing fluid communication between a passageway 66 in the tip 18 and the passageway 36. To minimize any flow restriction, the passageway 36 adjacent the tip 12 is preferably open to the passageway 16 without any secondary valves or other obstructions to fluid flow. The upper portion 38 of the septum 28 pivotally deforms downward, stretches and extends along the annular skirt 52 and the outer surface 68 of tip. In addition the lower portion 40 of the septum 28 extends downward and stretches about the outer surface 68, and establishes a seal about the tip 18.

Referring briefly back to FIG. 1, upon removal of the tip 18, the septum 28 resiliently retracts into its closed position.

When the tip 18 is inserted into the connector 10 to the desired depth D, there is a limited amount of annular space between the housing 26 and tip into which portions of the septum 28 may be displaced; however, the septum must be configured and sized to seal before, during and after extension of the penetrating member 12 through the opening 44 to form a closed system.

Referring to FIGS. 1 and 2, in several applications in the medical environment, it is highly desirable that connectors be configured to seal against a pressure of 20 psi. As noted above, in various connector designs using a pre-slit septum and blunt cannula penetrating member, as described in U.S. Pat. No. 5,135,489, incorporated by reference herein, the sealing is accomplished by utilizing a thickened septum and a housing to radially compress the septum thereby sealing a slit extending through the septum. When a blunt cannula of small diameter is forced through the slit, the septum is additionally radially compressed which seals about the cannula, and there appears to be little displacement of portions of the septum in an axial direction.

However, even if a luer tip 18, with its much wider diameter relative to the housing opening than the blunt cannula relative to the corresponding housing opening, could be forced through the slit in such a septum, there is little room in the radial direction to provide a receiving space for the displaced mass of the septum. Thus, the necessary insertion force would likely be too much for most medical practitioners. However, it has been found that thinning the septum 28 to allow displacement and accommodation of the septum between the tip and housing while maintaining the same radial compression does not provide the septum with the ability to seal against a pressure found in fluid passageways i.e. "leak pressure", found during intravenous therapy. Unexpectedly, increasing the radial compression of the thinned septum does not appear to provide a corresponding rate of increase in the leak pressure of the connector 10.

Forming the septum 28 with a thinned upper portion 38 and a downwardly extending lower portion 40 and providing that the opening 44 extends downward through the lower portion 40 in addition to the upper portion 38 greatly increases the leak pressure without requiring a corresponding large increase in septum thickness or compression. Moreover, tests have shown that the length "L1"(FIG. 3) of the lower portion 40 is related to increasing the leak pressure. But, increasing the mass of the septum 28 by increasing the length L1 of the lower portion 40 which must be accommodated within the housing 26 when a luer tip 18 penetrates the resealing member 28, increases the insert force and could possibly prevent the tip 18 from extending entirely through the opening 44.

The first embodiment's configuration of a unique combination with a predetermined length L1 of the lower portion 40, thickness and compression of the upper portion 38 gives the connector 10 a leak pressure of more than 20 p.s.i while presenting an acceptable insert force. Other features of the configuration of the first embodiment is the ability to provide a reseal, after multiple insertions of the luer tip and long periods of luer tip indwell, against a pressure of 6 p.s.i.

As an example, in the first embodiment, forming the septum with the upper portion 38 having a thickness of 0.040 inches and a 3.5% radial compression or greater and the lower portion 40 having a length L1 of about 0.080 inches (giving rise to a opening length of 0.125 inches) yields a connector 10 which may accept the luer tip 18 to the desired depth D while maintain a leak pressure in excess of 20 p.s.i.

Referring in particular to FIGS. 3 and 3a, preferably the lower portion 38 is formed with a width "W1" of approximately 0.060 inches and a length "L2" of about 0.190 inches. The annular skirt 52 is formed with a thickness of about 0.010 inches. The top surface 70 of the septum 28 is slightly concave to lessen the amount of material being forced into the housing 26 upon insertion of the tip 18 through the opening 44. It is envisioned that the top surface 70 may be flat or have a convex surface or a combination, also. In addition, the top surface 70 is formed unbroken without crevices or other pockets which facilitates disinfecting of the septum 28 with normal aseptic techniques such as swabbing. Also the septum 28 is formed so that the top surface extends completely over the upper end 30 of the housing to present a visually appealing top surface.

Referring back to FIG. 1, to be able to accommodate the standard dimensions of luer fittings, the housing 26 is configured to form a passageway having a diameter "D1" of 0.235 inches. To facilitate insertion of the septum 28 during assembly, the upper end of the passageway 36 is tapered outward so that a slightly larger diameter of 0.250 inches is formed at the opening 32.

Referring to FIG. 2, as can be appreciated, inserting the tip 18 and compressing the upper portion 38 and possibly the lower portion against the annular skirt 52 should produce a thickness layer of at least 0.050 and 0.040 inches respectively. However, when inserting one embodiment of a penetrating member 12 having standard luer dimensions to a desired depth D of 0.300 inches should only provide an annular clearance of 0.030 inches between the tip and housing 26. Unexpectedly, the elastic material of the septum elongates upon stretching and deforms into this small clearance dimension, while not exhibiting too low a leak pressure after long periods of indwell due to compression set of the septum 28.

Referring again to FIG. 3a, the lower portion 40 is formed with rounded corners 74 to form a gap 77 between the lower portion and skirt 52. The rounding of the corners 74 allows the sidewalls 48 and slit 46 to be as long as possible while still providing the gap between the lower portion 40 and skirt 52. Attaching the sidewalls 48 to the skirt 52 without providing a gap may contribute to unequal stretching and deformation of the lower portion 40 about the tip 18 during insertion of the tip resulting in leakage. To create the gap 77 the valve member 27 at the gap 77 has a vertical thickness less than the length L1 of the lower portion. Preferably the gap 77 is formed such that the vertical thickness of the valve member 27 at the gap is equal to the thickness of the upper portion 38 of the septum 28.

At the juncture between the central portion 34 and skirt 52 a sharp corner is formed which establishes a hinge point 78. The hinge point 78 which extends about the housing for the entire circumference of the opening 32 also facilitates the flexing and deformation of the septum 28 during insertion of the tip 18.

In an embodiment, the septum 28 is formed of a elastic, resilient material provided by the West Company of Lionville, Pa. It is anticipated that lubricating the septum 28 should facilitate insertion of the luer tip 18. Such lubrication may be applied while forming the slit or by other means such as incorporating the lubrication into the septum material or by applying lubricious coatings to the top surface. In a second embodiment, the septum 28 may be formed of a similar material, such as chlorinated polyisoprene produced by Lexington Medical of Rock Hill, S.C. In addition, the slit may be lubricated after assembly of the housing and septum using silicon oil produced by Dow Corning of Midland, Mich. The housing 26 is rigid and preferably formed of DN003 from Eastar of Kingsport, Tenn.

Figure 6:
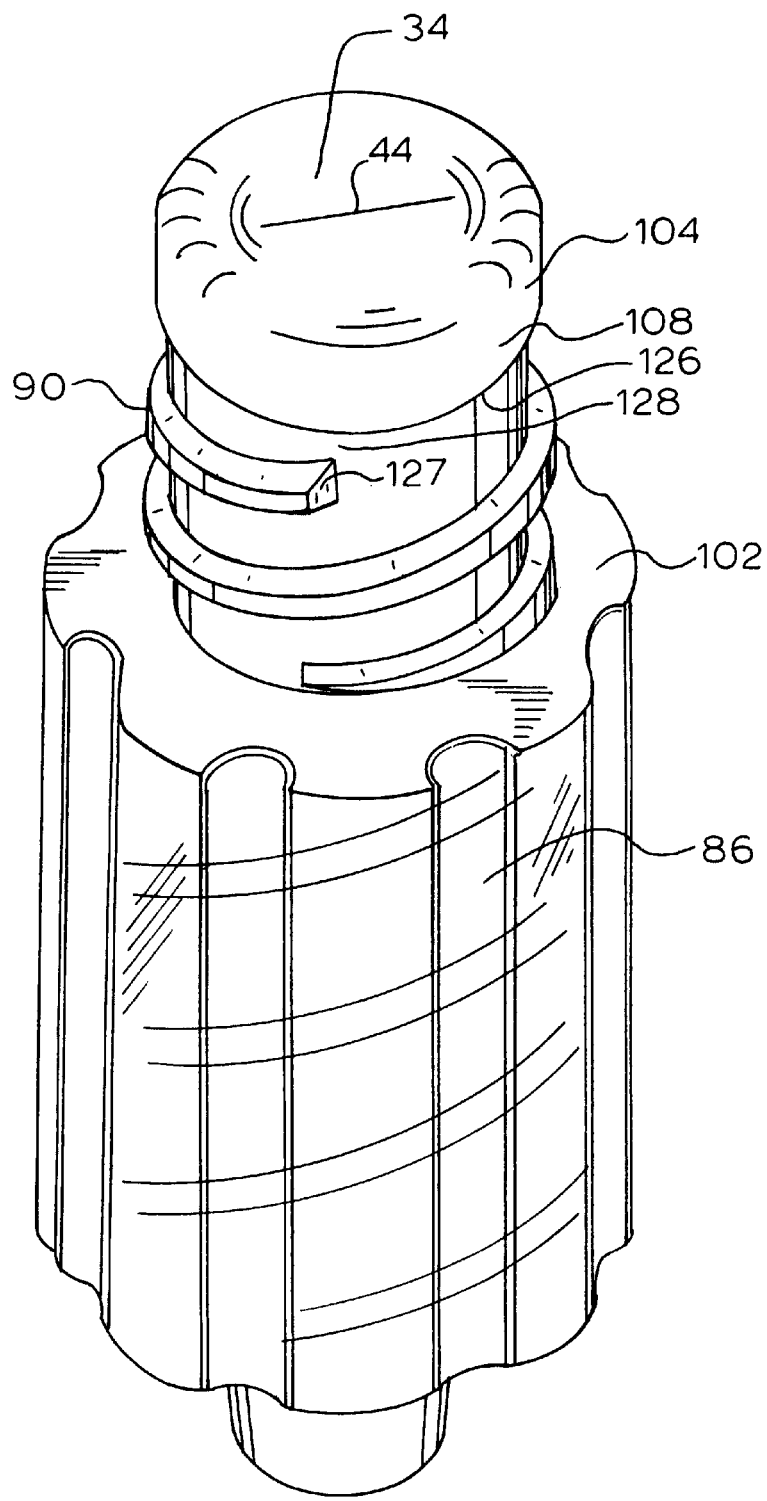
FIG. 6 is a perspective view of the connector of FIG. 4.

Although the housing 26 is shown as forming a luer connection 84 at a lower end, the housing may also be formed as a part of any device into which is it desirable to establish a sealed connection such as the injection arm of a Y-site 86 (FIG. 7), as an inlet on a stopcock or manifold (not shown) or the like. In addition the lower end of the housing 26 may be integrally formed with a catheter 15 with a guidewire (not shown) extending upward through the opening 44. Referring also to FIG. 6, particularly when used as an injection site for a catheter 15, the exterior of the housing 26 is formed with a number of longitudinally extending indentations 86 which facilitate gripping of the connector 10.

Figure 4:
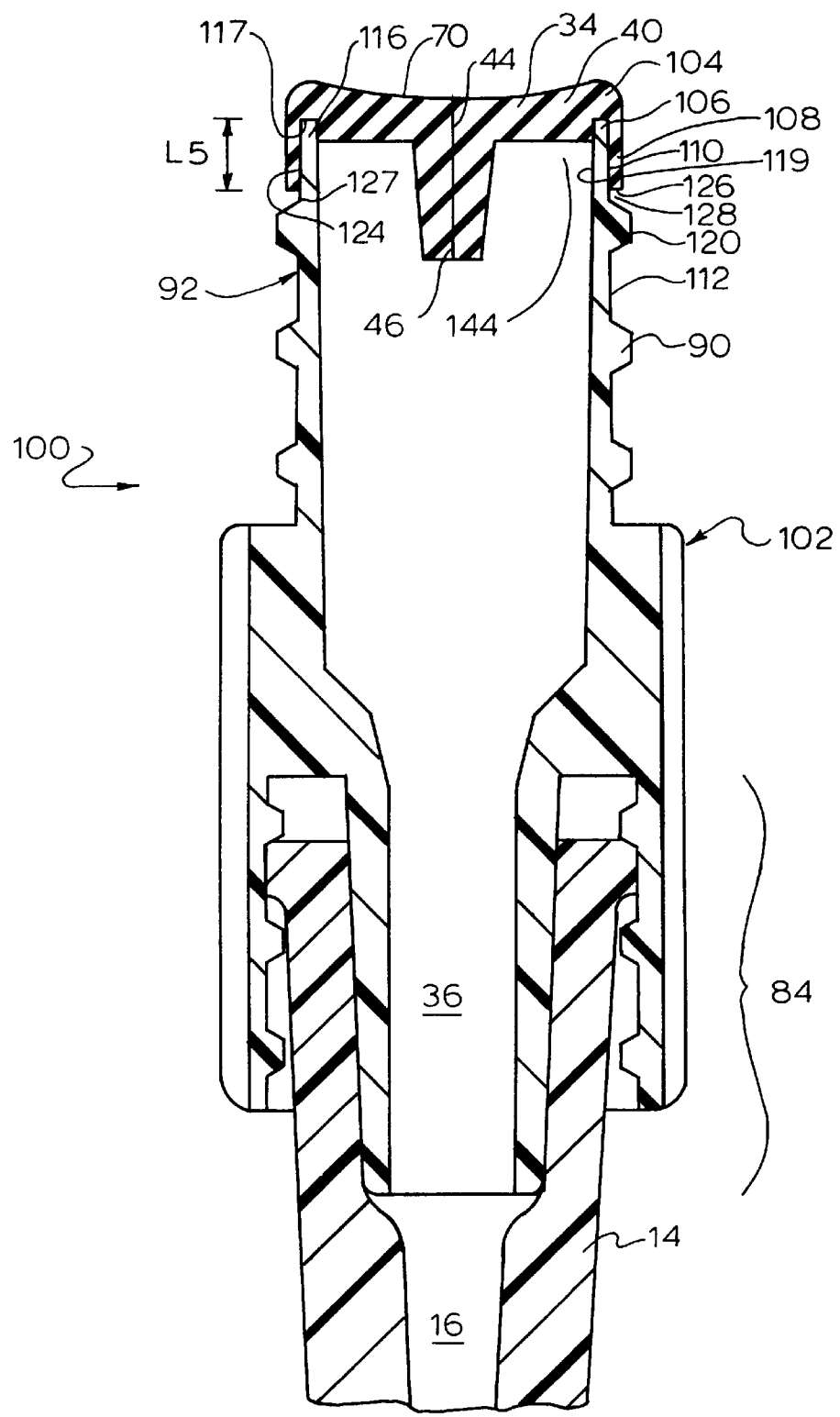
FIG. 4 is a section view of a second embodiment of a needleless connector of the present invention.

Referring to FIG. 1, to provide for a threaded engagement with a locking flange 20 the upper end 30 of the housing 26 may be formed with a pair of radially extending ears 88 configured to engage the threads 64. Referring to FIG. 4, alternately threads 90 may be formed on that portion 92 of the housing 26 which will engage the threads 64 on the flange 20.

Preferably the housing 26 is molded as a single piece utilizing molds with a large number of molding cavities to facilitate high speed manufacturing operation. Similarly the valve member 27 is preferably formed as a single piece in a high speed molding operation, and the shape of the lower portion 40 is particularly suited to register the valve member 27 in a desired orientation for fashioning an opening 44 therein.

Figure 5:
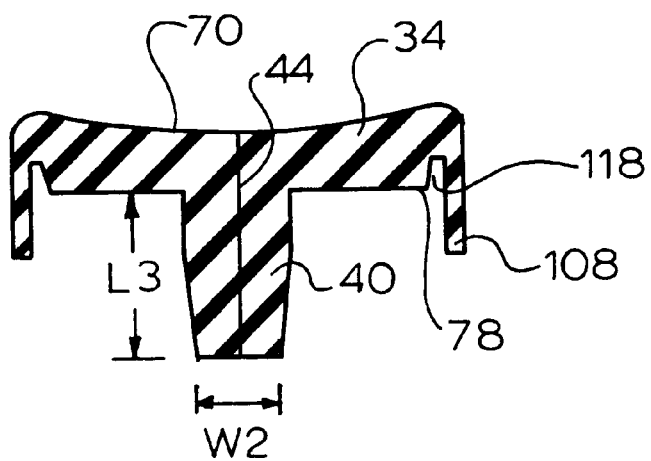
FIG. 5 is a section view of a septum forming a part of the connector of FIG. 4.

Referring to FIGS. 4–6, a second embodiment of the needleless connector of the present invention is generally indicated at 100 and is particularly suited to a large number of connections and disconnects with a standard male luer lock 13 (FIG. 2) without unacceptable leakage. In addition, elements in the second embodiment corresponding to elements in the first embodiment 10 are labeled with the same reference number.

The connector 100 includes a housing 102 and an elastic and resilient resealable valve member 104 disposed at an upper end 106 of the housing. The valve member 104 includes the central portion 34 and lower portion 44; however the valve member 104, preferably a septum 105, also includes an annular skirt portion 108 which extends about and surrounds an upper portion 110 of the housing 102 adjacent the upper end 106. Preferably the skirt 108 is bonded to the exterior surface 112 in a specified manner to attach the valve 104 to the housing 102 and elastically restrain the central portion 34 during insertion of the luer tip 18 (FIG. 2).

Figure 5A:
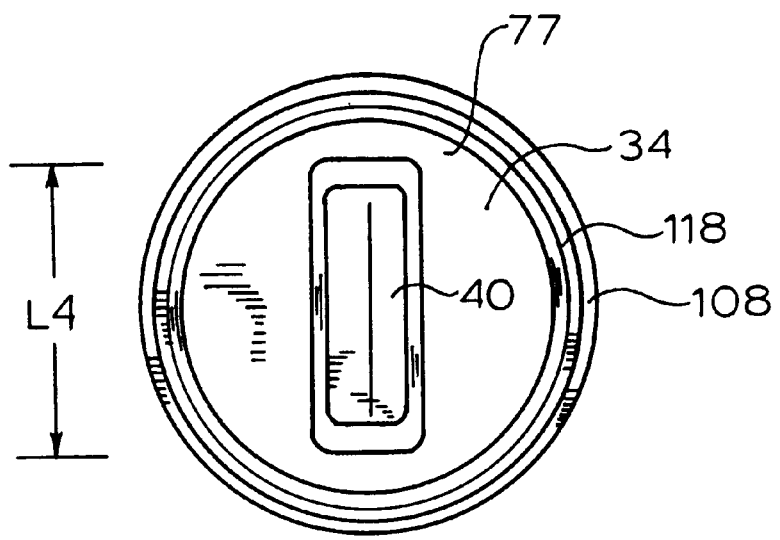
FIG. 5a is a bottom plan view of a septum forming a part of the connector of FIG. 4.

Referring to FIGS. 4, 5 and 5*a*, it has been found that the manner in which the valve 104 is configured relative to and attached to the housing 102 has an important effect on the ability of the connector 100 to achieve the desired performance standards. Preferably the valve 104 defines a circular annular receiving channel 118 between the central portion 34 and the skirt 108. The upper end 106 of the housing 102 is received in the channel 118 and bonded to the valve 104 in a desired manner.

The central portion 34 is configured such that the upper edge portion 106 applies a 6 to 7% compression on the central portion. To provide adequate reseal, it is desired that the upper portion 40 of the valve 102 form a thickness of 0.60 to 0.50 inches and the lower portion define a length L3 of 0.080 inches.

Preferably the lower portion 40 is formed with a width "W2" of approximately 0.060 inches and a length "L4" of about 0.165 inches. The annular skirt 108 is formed with a thickness of about 0.010 inches. The top surface 70 of the septum 28 is slightly concave to lessen the amount of material being forced into the housing 102 upon insertion of the tip 18 (FIG. 2) through the opening 44. It is envisioned that the top surface 70 may be flat or have a convex surface or a combination, and is adapted to disinfecting techniques such as swabbing.

At the interface between the central portion 34 and upper end 106 of the housing 102, the valve member 104 forms a sharp corner and thereby forms a hinge point 78. Similar to the first embodiment 10, lower portion 40 is spaced from the housing to form a gap 77.

It has been found that bonding an upper landing 117 defined by an upper edge 116 to the valve 104 and about the entire circumference of the of the upper edge is important in the ability of the connector 100 to maintain a satisfactory leak pressure and increasingly important to maintain the leak pressure after 100 or more connections and disconnects. The bonding also anchors the septum 28 to the upper edge and prevents a rubbing between the septum 28 and upper edge 116 as the septum is elastically stretched during insertion of the tip 18.

Bonding between the exterior surface 112 and the inner surface of the skirt 108 is also important, but migration of any bonding agent to the interface between the central portion 34 and housing 102 should be minimized. If adhesive collects in the interface about the septum 28 and interior surface 119 cracking of the housing 102 or compression set of the septum 28 with corresponding leakage after long periods of indwell may result.

One preferred method of applying bonding agent to the housing 102 such that the upper landing 117 and exterior surface 112 receive such agent while minimizing migration to the interior of the housing is minimized is by placing the housing 102 is a vertical position with the upper edge 116 facing downwards. Bonding agent is applied, preferably by injection, to the exterior surface 112 and gravity causes the agent to flow down and wet the landing 117. Gravity also hinders any migration of the bonding agent into the interior surface of the housing 102. A further preferred step includes inserting the upper end portion 110 of the housing 102 into a chamber (not shown) and applying a negative air pressure below the housing 102 such that air flows downward along the housing which also hinders migration of the bonding agent upwards into the interior of the housing.

It has been found that a UV curing adhesive, such as Loctite 3011, 3311 and 3301 from Loctite Corporation of Rocky Hill, Conn. may be utilized as a suitable bonding agent for any of the connectors 10, 100, 200. The bonding agent should be cured for a sufficiently long period of time.

Referring to FIGS. 4 and 6, to provide for threaded engagement with the locking flange 20, threads 90 extend along a portion of the exterior surface 112. The upper end 127 of the threads 90 are spaced from the upper edge 116 of the housing 102 to form a surface 124 free of threads, ridges or the like to facilitate the bonding of the skirt 108 to the surface 124. In a preferred embodiment the surface 124 is also formed with very little if any draft or taper so that the skirt 108 does not creep upward during setting of the bond between the valve 104 and housing 102. Preferably the skirt 108 extends downward along the housing 124 for a length L5 of about 0.07 to 0.08 inches.

Referring also to FIG. 2, to minimize shredding of a lower edge 126 of the skirt 108 by the threads 64 on the locking flange 20 during removal of the penetrating member 12 it is important that such threads do not catch on the edge 126. Thus it is desired that the lower edge 126 be separated from the upper edge 127 of the threads 90 such that the width of a defined gap 128 is less than the width of the threads 64.

To facilitate a releasable engagement of the penetrating member 12 to the connector 100 and to minimize or eliminate any shredding of the skirt 108, the skirt 108 may be provided with a thickness such that there is minimal interference between the skirt 108 and the inner edge surfaces 64a of the threads 64 on the locking flange 20. However the smaller the diameter defined by the skirt 108 with a given skirt thickness and housing thickness, the smaller the volume which must accommodate both the penetrating member 12 and valve 104 upon insertion of the member 12.

It has been found that providing a housing 102 with the upper portion 110 having a external diameter of 0.25 inches and defining an opening 144 with a diameter of 0.22 is desired to provide the proper clearance between the skirt 108 and locking flange 20 of an ISO standard luer connection and yet also provide a housing with sufficient wall strength to resist fracture and provide sufficient space for the displaced septum 28 and luer tip 18 when the luer tip is inserted into the housing 102.

Referring to FIG. 4 in conjunction with FIG. 2, the frustoconical shape of an ISO standard luer tip defines a diameter ranging from 0.155 in. to 0.175 inches. Thus when an ISO standard luer tip 18 is inserted the desired insertion distance D, it would be expected that the tip and housing 102 define a clearance therebetween of 0.031 to 0.021 inches. What is surprising is that upon insertion of a male luer tip 18, the valve 102 having an upper portion 38 with a thickness of about 0.055 inches extends about the luer tip and is compressed within the smaller clearance without requiring an unacceptable insertion force. In addition, although one may expect some compression set of the septum 28 due to the compression between the tip and housing which would lead to leakage after long indwell problems, it has been unexpectedly found that the valve member 104 maintains an adequate leak pressure after long periods of indwell.

Figure 7:
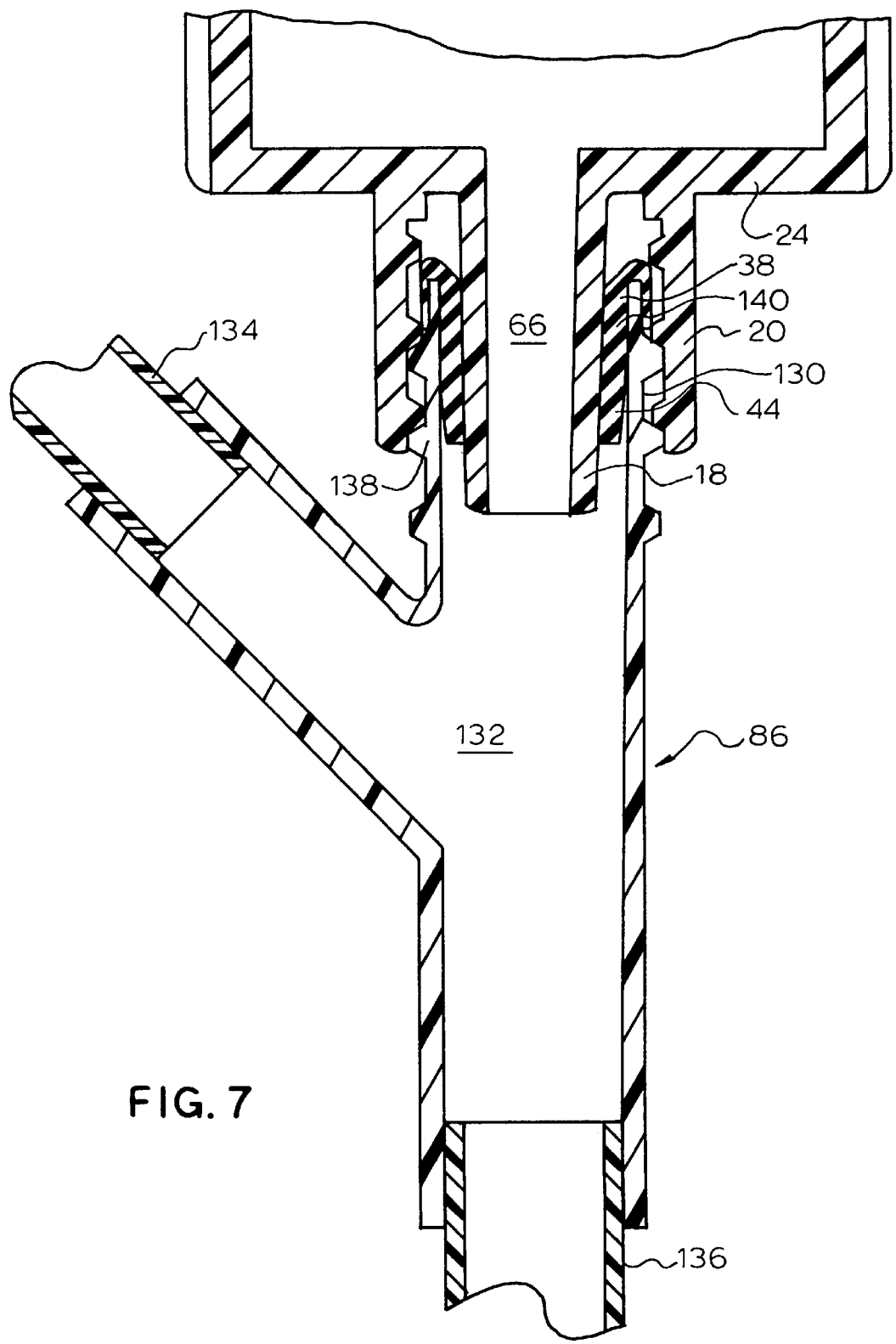
FIG. 7 is a sectional view of a connector similar to the connector shown in FIG. 4 included as a part of a Y-site.

As illustrated in FIG. 7, the displacement and compression of the septum 28 into the space between the tip 18 and housing 102 during insertion of the tip substantially fills the space between the lower portion 40 and housing 102 for a depth corresponding to the majority of the extended length of the lower portion about the tip 18. The compressed septum 28 displaces or flushes any fluid that has collected in this space. The injection of the fluid from the tip 18 into the interior of the housing 102 flushes any remaining spaces within the housing. Thus stagnant pockets of fluid are avoided. The filling of the passageway 36 with the tip 18 and displaced septum 104 also reduces priming volume to a low level.

Referring to FIG. 7, an embodiment of the needleless connector of the present invention is generally illustrated at 130. In particular the connector 130 is shown as forming part of a Y-site connection assembly 86. As is generally known in the field, Y-site connection assemblies 86 are particularly suited for adding supplemental fluid to a flow of fluid along a primary flow path 132 extending from an upper or entry section 134 of attached tubing, through the Y-site assembly 86 and out along a lower or exit section 136 of attached tubing.

The needleless connector 130 is shown as generally corresponding to the second embodiment of the needleless connector 100, however, the resealable valve member 140 and housing 138 proximate the valve member may be shaped to correspond to the housing and valve member of either the first embodiment 10, second embodiment 100 or the later described embodiment 200.

As can be appreciated, once the luer tip 18 penetrates the valve member 140, the passageway 66 in the tip is placed directly in fluid communication with that portion of the primary flow path 132 extending into the exit section 136 without any intermediate valves so any flow restriction is reduced.

Figure 8:
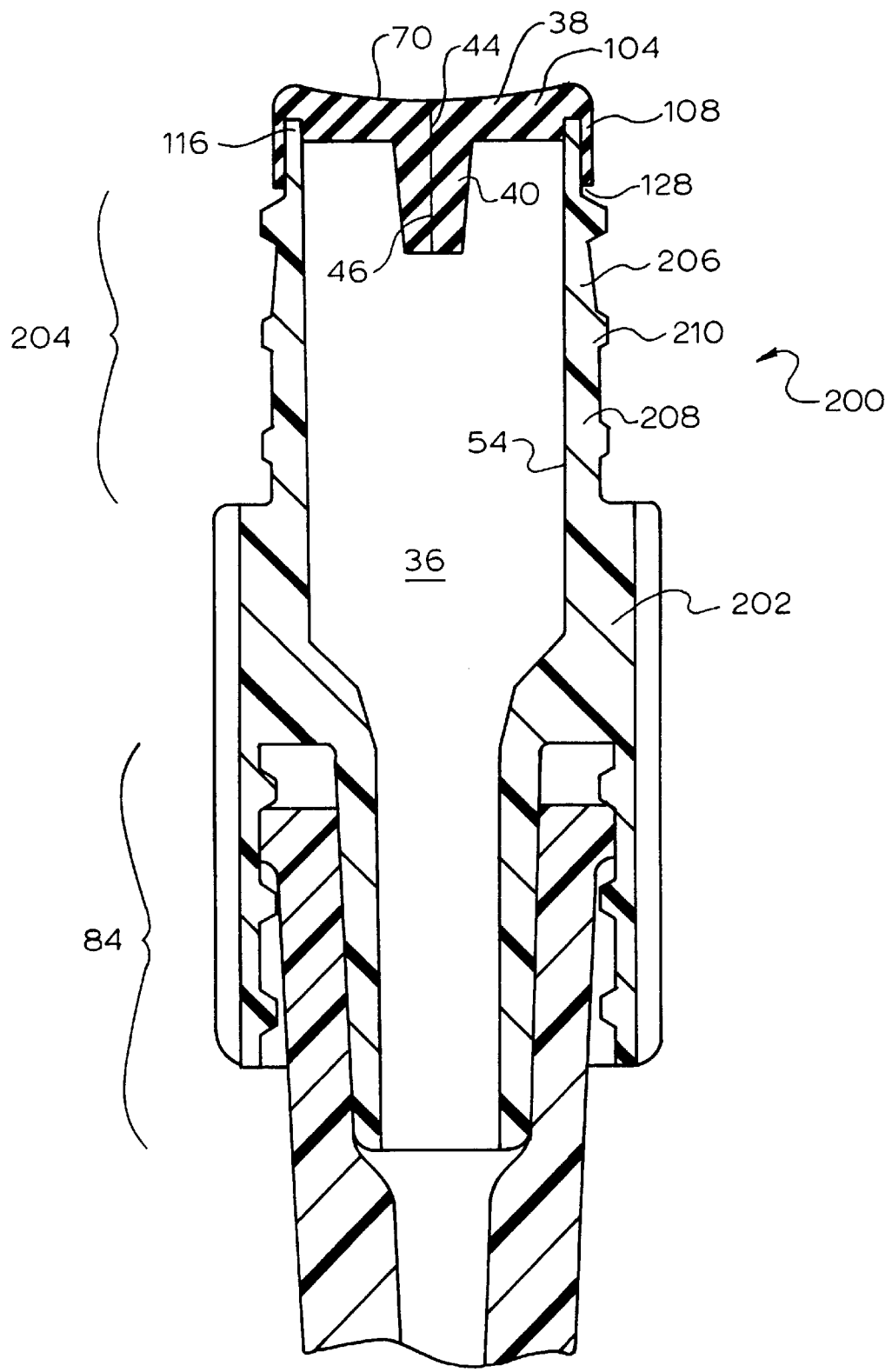
FIG. 8 is a third embodiment of the needleless connector of the present invention.

Referring to FIG. 8, a third embodiment of the needleless connector of the present invention which is preferred, is generally indicated at 200. The third embodiment 200 has a housing 202 and includes the resealable valve member 104 described in relation to the second embodiment 100. The housing 202 is similar to the first embodiment 100 except that a housing portion 204 below the gap 128 has been altered so that connector 200 provides a higher removal resistance torque. Elements in the third embodiment 100 corresponding to elements in the first or second embodiment 10 are labeled with the same reference number.

In particular, the housing 202 includes the upper portion 110 having the surface 124 of a generally constant outside diameter over which the skirt 108 extends. A middle portion 206 extends downward from the upper portion 116 and a lower portion 208 extends downward from the middle portion. The lower portion 208 preferably defines a generally constant diameter greater than the diameter defined by the upper portion 116. The middle portion 206 is formed to provide a transition from the upper portion 116 to the relatively wider lower portion 208. Preferably the middle portion 206 is frustoconically shaped.

Referring to FIGS. 2 and 8, the housing 202 defines a set of double start threads 210 which extend downward along the housing about the middle portion 206 and lower portion 208. In the preferred configuration, the threads 210 define a constant major diameter as the threads extend along the lower and middle portions such that the height of the threads decreases as the threads move downward along the middle portion. However the diameter defined by the lower portion 208 is greater than the minor diameter defined by the internal threads 64 on the locking flange 20 such that there is a sliding frictional engagement between the threads 64 and middle and lower portions 206, 208. The frictional engagement allows the connector 200 to provide an acceptable removal resistance torque for an attached luer lock when the tip 18 has penetrated to the desired insertion depth D.

Utilization of an upper portion with a surrounding skirt 108 defining a diameter approximately that of the standard major diameter of threads 64, a frustoconical middle portion 206 defining a diameter increasing from a diameter less than the diameter defined by the skirt 108 to the diameter of the lower portion 208 and the lower portion defining a diameter greater than the minor diameter of the internal threads 64 imparts a feel to the user similar to connecting to a standard female luer connection.

When the user first inserts the locking flange 20 over the connector 200, slipping the flange over the upper portion 116 and surrounding skirt 108 promotes centering of the luer tip 18 relative to the connector 200 and minimizes the opportunity for cross threading. As the tip and flange 20 continue over the connector 200, the threads 64 then engage the threads 210 and the connector 200 must then be rotated relative to the flange 20 to threadingly engage the flange 20 to the connector 200.

During rotation, the tip 18 extends through the opening 44 and rubs against the valve 104 however such contact supplies very little resistance to turning. The threads 64 engage the middle portion 206 and a sliding frictional engagement begins and the required torque to advance or unthread slowly increases as the tip is rotatably advanced. The threads 64 then engage the lower portion 208 having a constant diameter which slows down the rate or increase in the removal torque before an unacceptable removal torque is achieved which may cause the locking flange 20 to lock up on the connector.

In addition male luer locks 13 may be made of many different types of materials which range in stiffness. It is important that the connection of the connector 200 to the luer lock not place such a stress on the locking flange 20 which may fracture the flange. The use of the lower portion 208 with a constant diameter also accommodates luer locks of various materials while preventing overstressing of the locking flange 20.

Thus five example embodiments of a needleless connector have been described. It is believed that the embodiments provide features which solve many of the drawbacks which have hindered widespread acceptance of such needleless connectors relative to the market acceptance of the type of connectors which must be pierced with a sharp needle or blunt cannula.

Figure 9:
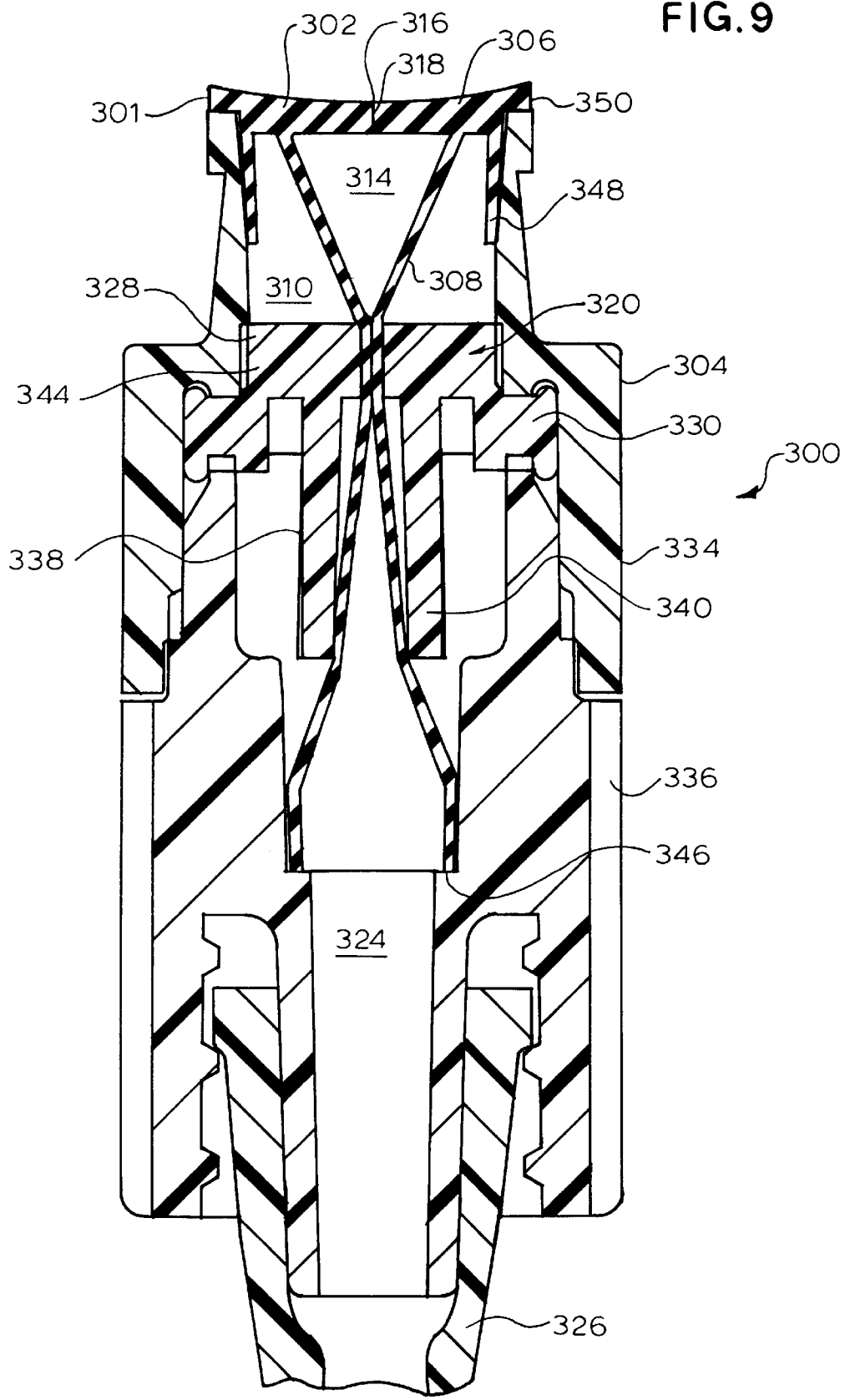
FIG. 9 is a section view of an alternate embodiment of a needleless connector of the present invention.
Figure 10:
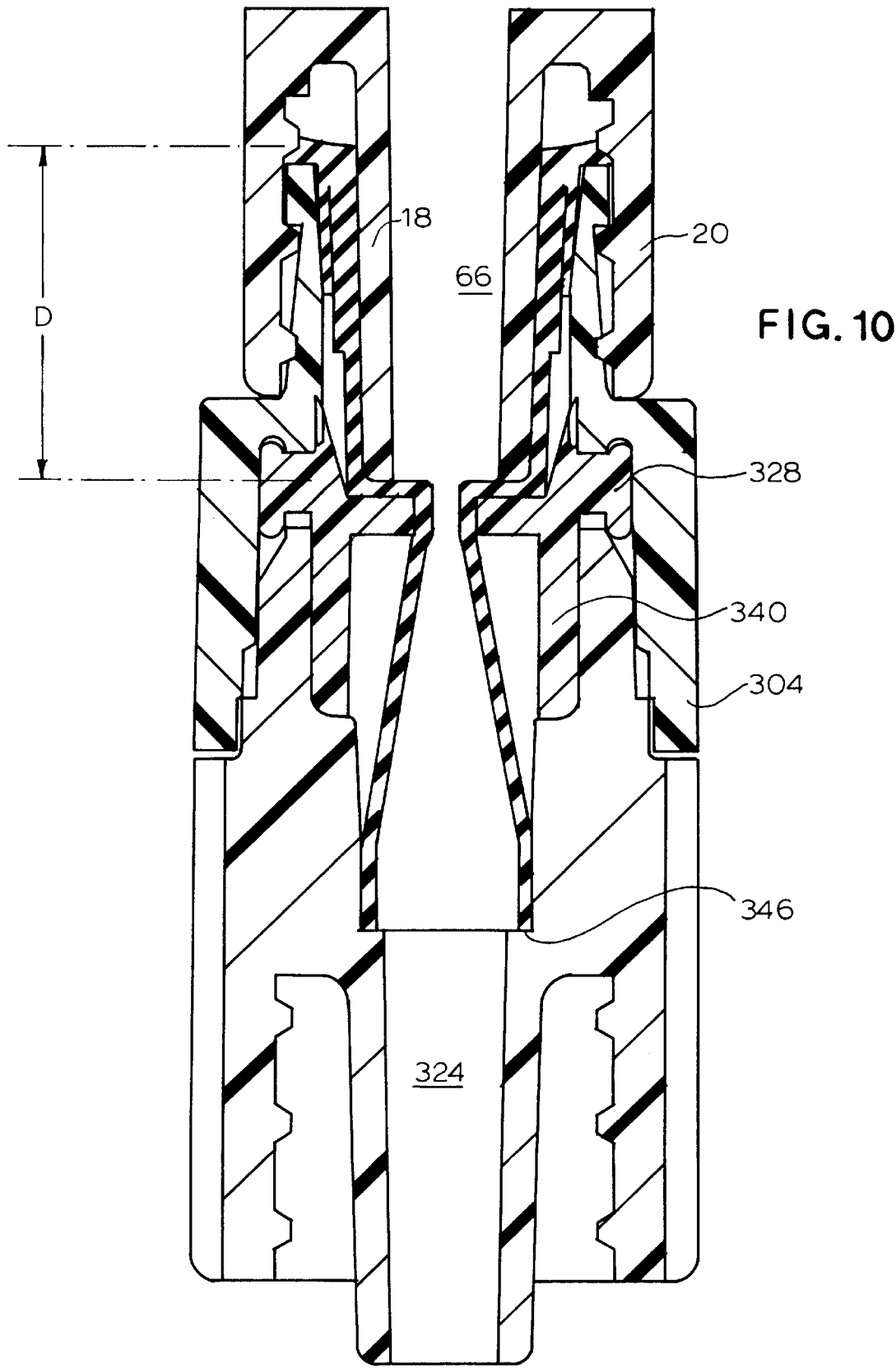
FIG. 10 is a section view of the connector of FIG. 9 shown connected to a male luer tip.

Referring to FIG. 9, an alternate embodiment of the connector uniquely suited to handling higher leak pressures is generally indicated at 300. The connector 300 includes an elastic resealable member 301 such as a septum 302 attached to a housing 304. The septum 302 includes a generally disk shaped upper portion 306 and a generally tubular extension 308 depending downward within a passageway 310 formed by the housing 304. The extension 308 is attached to the housing 304 to form a sealed conduit 314 for the transmission of fluids injected through an opening 316, preferably a slit 318, extending through the upper portion 306.

Referring briefly to FIG. 1 also, in a manner similar to the septum 28, the opening 316 may extend partially through the septum 302 with the anticipation that the opening will extend completely through the septum upon penetration by the luer tip 18. In addition, the upper portion 306 may be formed in a manner similar to the upper portion 38 of septum 28.

A valve element, generally indicated at 320, provides at least one seal against pressurized fluid within an exit passageway 324 formed by portions of the extension 308 and housing 304. The exit passageway 324 is in fluid communication with a device 326 in fluid communication with a body. The device 326 may include a catheter or an I.V. administration set. If the connector 300 is for providing a resealable connection with an I.V. administration set, the housing 304 will preferably form a portion of a Y-site.

The valve 320 includes a pincher portion 328 which pinchingly deforms the extension 308 to seal against leak pressure found in the exit passageway 324. The pincher portion 328 is attached to the housing 304 by fixedly clamping a peripheral edge 330 between an upper housing piece 334 and a lower housing piece 336 which are bonded together to form the housing 304.

The connector 300 also includes an extension collapsing element 338 which contacts and partially collapses a portion of the extension 308 after and possibly during the sealing of the extension by the valve 320. The partial collapsing produces an expelling of fluid from the exit passageway 324 after the sealing of the extension by the valve 320.

Referring also to FIG. 5, in the preferred embodiment, the collapsing element 338 is connected to, by being integrally formed as a portion of, the valve 320. The collapsing element 338 includes two legs 340 connected to and extending downward and outward from the pincher portion 328. The legs 340 extend on opposite sides of the extension 338 and contact the extension deforming the extension radially inward. When a luer tip 18 penetrates the septum 302 by extending through the opening 316, to the desired depth D, the tip contacts the pincher portion 328 displacing it downward and opening the element to place the passageway 66 in fluid communication with the exit passageway 324. The legs 340 are also forced radially outward against the housing 304 allowing the extension 308 to expand. During removal of the tip 18, the pincher portion 328 of the valve 320 closes, initially sealing the extension 308, and then the legs 340 continue to collapse the extension 308 below the pincher portion forcing a portion of the fluid out of the exit passageway 324 into the device 326.

To place the pincher portion 328 in a better position for contact and activation by the luer tip 18, the valve 320 may be formed with a central portion 344 offset upward of the peripheral edge 330. The legs 340 are attached to this central portion 344; however, the legs may be attached to other parts of the housing 304.

To facilitate sealingly attaching the extension 308 to the housing 306, the lower piece 336 forms a radial lip 346, and the lower end of the extension is adhesively attached to the housing 305 proximate this lip. To hinder buckling of the extension 308 when the luer tip 18 forces the central part of the septum 302 downward, the extension may be stretched during assembly and attached to the housing in the stretched configuration.

Referring briefly to FIGS. 1 and 4, in a manner similar to the connector 10, the septum 302 of the connector 300 may include an annular skirt 348 and radial lip 350 which are bonded to the housing 304.

The attachment of the extension 308 to the upper portion 306 of the septum 302 and the housing 304 may help support the upper portion 306 against leaking due to pressurized fluid in the conduit 314. The extension 308 also prevents fluids from flowing into the housing outside of the extension an into areas which may be difficult to flush during use of the connector 300.

The septum 302 may also include a lower portion (not shown) similar to lower portion 40 (FIG. 3), but preferably the valve 320 provides most of the seal against leakage due to the pressure of fluid in the exit passageway 324.

Figure 11:
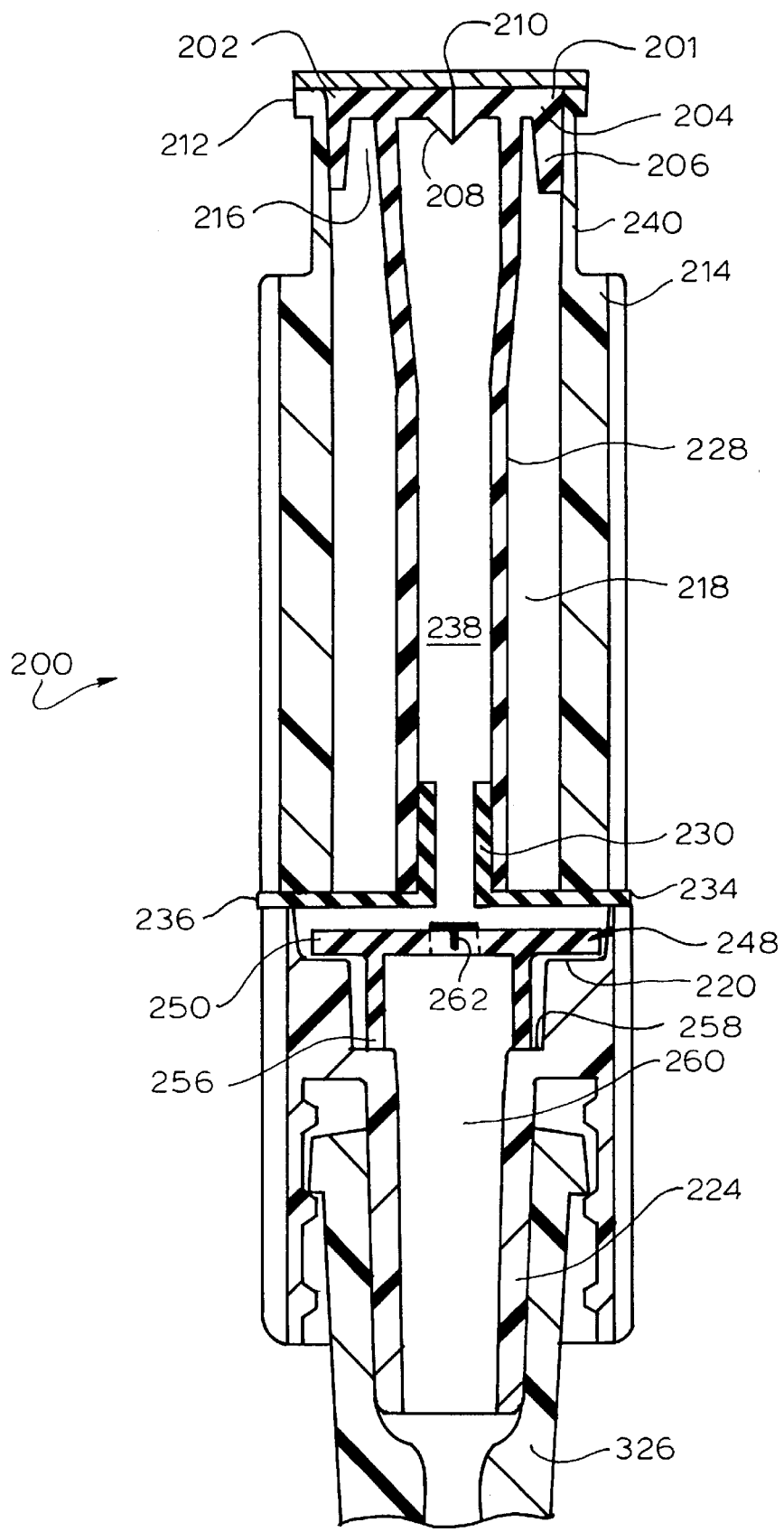
FIG. 11 is a section view of a further alternate embodiment of a needleless connector of the present invention.
Figure 12:
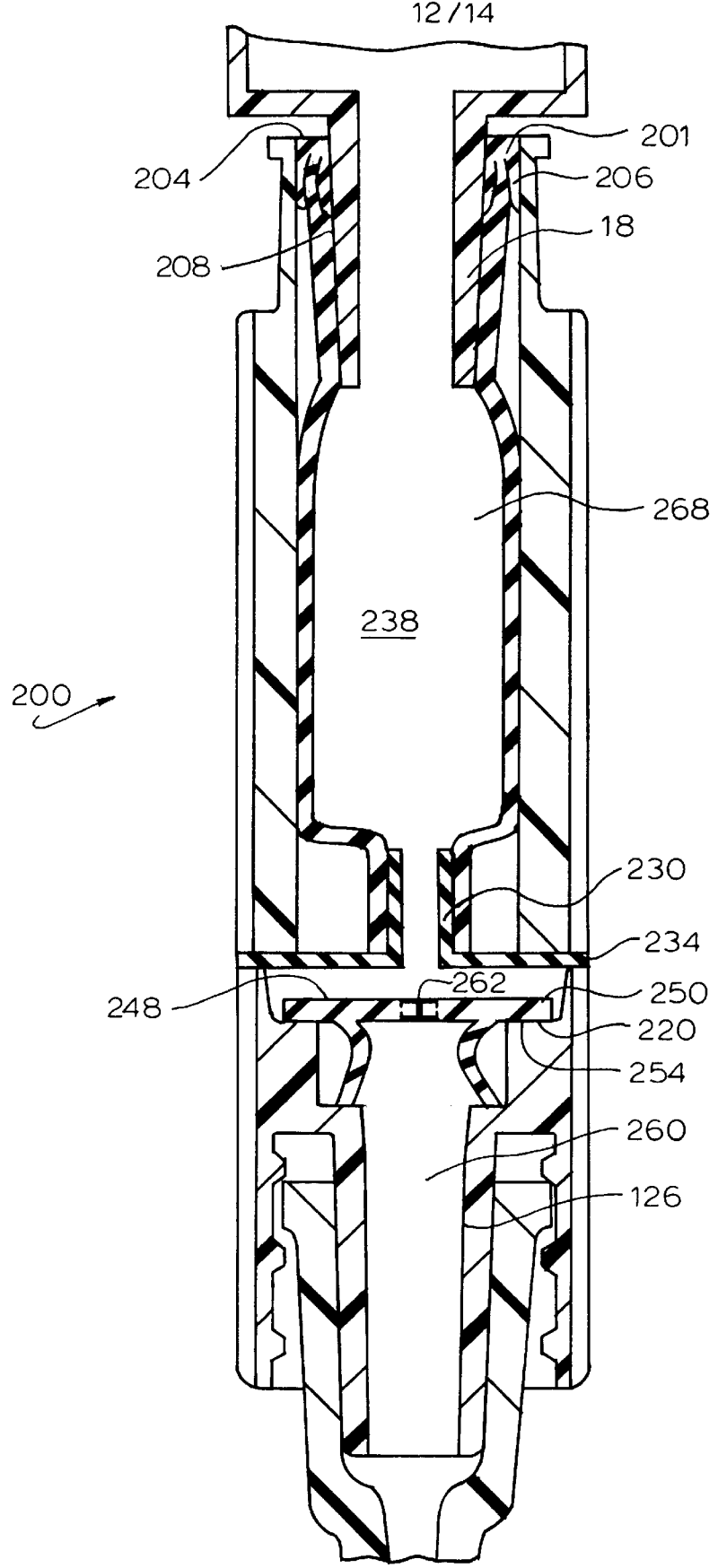
FIG. 12 is a section view of the connector of FIG. 11 shown connected to a male luer tip.

Referring to FIGS. 11 and 12, a further alternate embodiment of a connector uniquely suited to providing a flow of fluid into the device 326 after removal of the tip 18 is generally indicated at 200. Referring also to FIG. 1, the connector 200 includes a resealable member 201, preferably a septum 202 having an upper portion 204 similar in construction to upper portion 38, an annular skirt 206 similar in construction to the annular skirt 52, and a lower portion 208 and opening 210 similar in construction to the lower portion 40 and opening 44, respectively. The lower portion 208 is shown having a V shaped cross section; however, other configurations such as the configuration of lower portion 40 are also acceptable.

The septum 202 is attached to the top end 212 of housing 214 to seal an opening 216 formed by the top end. The housing forms an internal chamber 218 and a radially extending valve seat 220. A lower end 224 of the housing 214 is adapted to form a luer connection with the device 326 which is adapted to be placed in fluid communication with the body.

The septum 202 also includes a downward depending generally tubular extension 228 which extends to a point in reasonably close proximity with the valve seat 220. Sealingly attached to a lower end 230 of the extension 228 is a radial sealing flange 234. The flange 234 extends radially outward and forms a peripheral edge 236 which sealingly attaches to the housing 214. The septum 202 and flange 234 cooperate to prevent fluid flowing through a passageway 238 formed within the extension 228 from flowing into the chamber 218 outside of the extension and between the flange 234 and top end 240 of the housing.

Disposed within the housing 214 and about an outlet 240 of the chamber 218 is a valve 248. The valve 248 is uniquely configured to provide less fluid flow resistance when low pressure fluid is within the passageway 238 and high fluid flow resistance when high pressure fluid is within the passageway. Referring to FIGS. 6 and 7, the valve includes a radial sealing flange 250 having a peripheral portion 254 extending over the valve seat 220.

The valve 248 includes a set of downward depending legs 256 which contact a radial ledge 258 formed by the housing 214. The legs 256 are configured to support the flange 250 so that the peripheral edge 236 is spaced from the valve seat 220. Thus fluid may flow from the passageway 238 around the peripheral edge 254 and out an outlet 260 for the connector 200. The legs 256 are also configured to flex when fluid over a certain pressure is injected through the opening 210 and into the passageway 238 (as particularly illustrated in FIG. 12), the pressure of the fluid and the action of the fluid flowing around the peripheral portion 254 flexes the legs 256 and the flange 250 moves downward to seal against the valve seat 220.

The valve 248 also includes a capillary tube 262, preferably of a small diameter and constructed of metal, glass or the like, which extends through the flange 250 to form a passageway for a small flow of fluid from the passageway 238 into the outlet 260. The tube 262 is preferably sized so that the flow of fluid through the passageway is enough to maintain a KVO or keep vein open flow of fluid to the device 326.

Also when the luer tip 18 is inserted through the opening 210 and fluid is injected into the extension 228, the extension elastically expands in a radial direction to form a reservoir 268. The resiliency of the extension 228 maintains the fluid at a pressure sufficient to keep the flange 250 sealed against the seat 220 so that fluid only flows through the capillary tube 262. When sufficient fluid flows out of the reservoir 268 so that the extension 228 is in an almost deflated configuration, the pressure of the fluid in the passageway 238 drops to a level whereby the legs 256 straighten and the flange 250 separates from the valve seat 220 to allow much greater flow into the outlet 260.

Therefore it may be seen that by varying the configuration and material of the legs 256 in conjunction with the material of the extension 228, the pressure at which the valve 248 opens may be altered.

Figure 13:
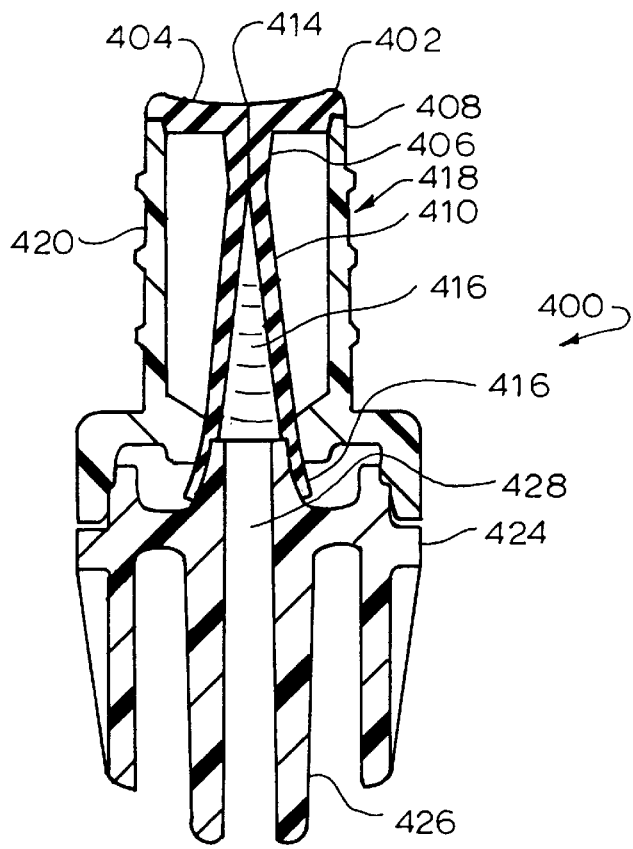
FIG. 13 is a section view of a further alternate embodiment of a needleless connector of the present invention.

Referring to FIG. 13 a further alternate embodiment of the needleless connector is generally indicated at 400. The connector 400 includes an elastic, resilient, resealable valve 402 having an upper portion 404, middle portion 406 and annular skirt 408 similar in configuration to the upper portion 38, lower portion 40 and annular skirt 108, respectively of connector 200 (FIG. 8). In addition the valve 402 includes a conically shaped tubular lower portion 410 integrally attached to the middle portion 406 such that an opening 414, preferably a slit, extends downward through the upper portion 404 and middle portion 404 into a chamber 416 defined in part by the lower portion 410.

A lower edge 417 of the lower portion 410 is sealingly engaged to a housing 418, preferably rigid, of the connector 400. In particular the housing 418 includes an upper portion 420 similar in configuration to the upper end of connector (FIG. 8) to supply the desired removal torque resistance capabilities. The housing also includes a lower portion 424 having a lower end 426 configured to establish a connection to a medical device (not shown) such as a catheter 15 (FIG. 1).

The lower edge 417 of the lower portion 410 extends about and is attached to an upwardly extending nipple 428. A collar 430 formed by the lower portion 424 of the housing 418 extends about the lower edge 417 and clamps the lower edge to the nipple 428. The lower portion 424 and upper portion 420 are attached to each other preferably by sonic welding or other appropriate type.

Figure 14:
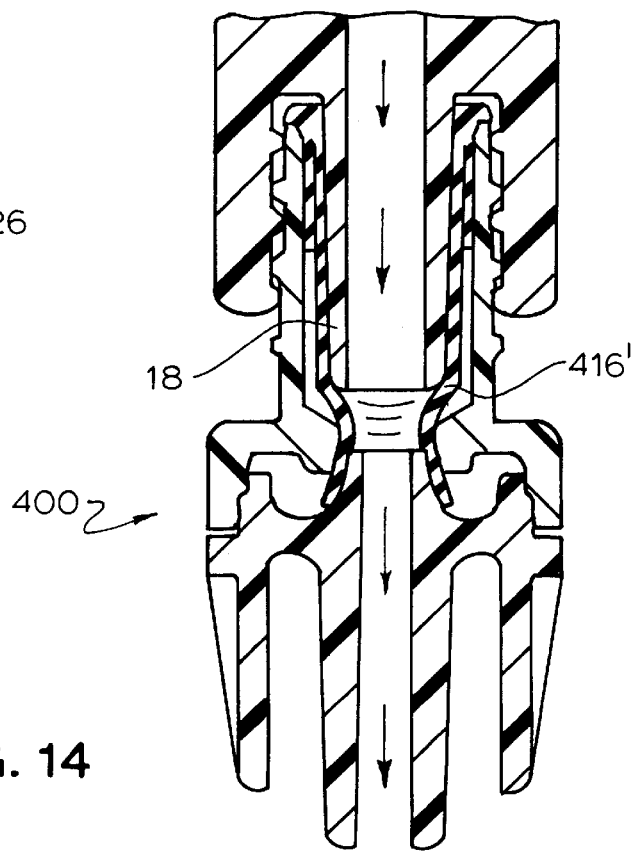
FIG. 14 is a section view of the connector of FIG. 13 shown connected to a male luer tip.

Referring to FIGS. 13 and 14, the connector 400 is particularly suited to eliminating voids and minimizing priming volume as the flow path is within the lower portion 410 of the valve 402 and fluid cannot flow into the space between the valve and upper housing. In addition, by appropriately dimensioning the valve 402, the chamber 416 defined by the lower portion 410 when no luer tip 18 is inserted into the connector 400, defines a volume which is less than the chamber 416' defined by the lower portion 410 when the luer tip is inserted. Thus siphoning of fluid into the chamber 416 upon removal of the tip 18 is avoided. Instead a slight flow of fluid from the chamber 416' through the lower end of the valve 426 upon removal of the tip 18 may occur.

Figure 15:
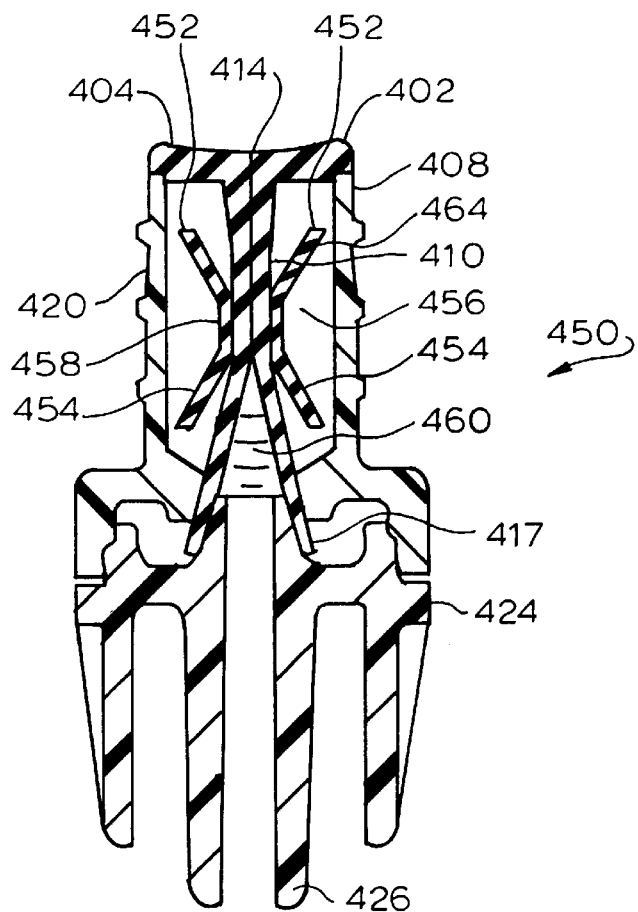
FIG. 15 is a section view of a further alternate embodiment of a needleless connector of the present invention.
Figure 16:
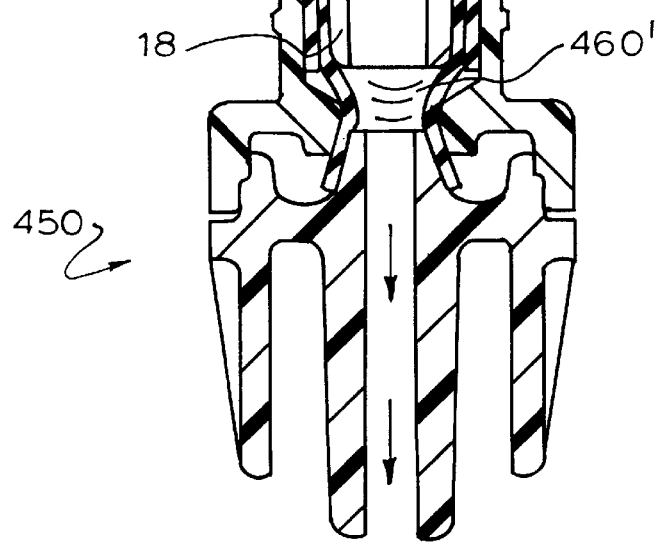
FIG. 16 is a section view of the connector of FIG. 15 shown connected to a male luer tip.

Referring to FIGS. 15 and 16 a needleless connector particularly suited to preventing siphoning upon removal of a luer tip 18 is generally indicated at 450. Preferably the connector 450 is similar to the connector 400 (FIG. 13) and elements in the connector 450 corresponding to elements in the connector 400 are labeled with the same reference number.

However connector 450 also includes a collapsing member 452, preferably a split collar 454 which is disposed in the void 456 between the lower portion 410 of the valve 402 and the upper portion 420 of the housing 418. The collapsing member 452 includes opposing inward landings 458 disposed on opposite sides of the lower portion 410 and engaging the lower portion to collapse the lower portion thereby lowering the volume of a chamber 460 defined by the lower portion. The landings 458 are resiliently supported by legs 464 angled in an outward direction. The collapsing member 452 may be composed of metal or other material which provides the desired resiliency in the legs 464.

Upon insertion of the luer tip 18, the luer tip 18 forces the landings 458 outward, bending the legs 464 so that the legs become generally aligned with the landings 458 and the lower portion 410 below the tip 18 defines the chamber 460'. Fluid may then be injected into the connector. Upon removal of the tip 18, the resiliency of the lower portion 410 will cause the lower portion to seek to assume the conical shape; however, the legs 464 will force the landings 458 inward to further collapse the lower portion such that the chamber 460 defined by the lower portion has a smaller volume than chamber 460'. Thus siphoning of fluid into the chamber 460 upon removal of the tip 18 is avoided and a slight volume of fluid is expelled from the chamber 460' through the lower end 426 upon the tip removal.

It will be understood that the embodiments of the present invention which have been described are illustrative of some of the applications of the principles of the present invention. Various modifications may be made by those skilled in the art without departing from the true spirit and scope of the invention.

What is claimed is:

1. A connector device for establishing a sealed connection with a male luer assembly configured to conform to ISO standards, said assembly including a male luer tip and having a generally annular flange disposed generally about said male luer tip and defining a generally cylindrical space between said flange and said tip, said connector device comprising:

a housing forming an upper opening and a central first passageway sized to receive the male luer tip, said housing having an upper end portion configured to fit with the space defined by the male luer assembly when the male luer tip is inserted downward into said opening, said first central passageway extending from said opening in a downward direction within said housing;

a resealable valve resiliently restrained relative to said housing, said valve including, a first portion configured to seal said opening prior to insertion of said tip and having an upper surface radially extending across said opening, said upper surface being disposed and shaped to be easily wipeable, a second portion integral with said first portion and extending generally vertically downward within said passageway from a lower surface of said first portion, and a third extension portion attached to a lower end of said second portion and extending downward from said second portion, a lower end portion of said third portion attached to said housing to form a sealed second passageway within said extension portion, said extension portion and said housing defining a generally annular space between said extension portion and said housing; and an opening formed in said valve such that when the luer tip is inserted downward into said opening in said housing and through said septum said first portion and said second portion elastically extend about the luer tip and form a seal about said luer tip and allow fluid to be injected from said tip into said second passageway, the attachment of said lower end of portion of said extension portion to said housing being such that fluid injected into said second passageway flows through said housing without flowing into said annular space.

2. The connector device of claim 1 wherein said valve includes a septum having an annular skirt integral with said first portion and extending over and attached to an outside surface of said housing proximate said opening to resiliently restrain said valve relative to said housing.

3. The connector device of claim 2 wherein said septum includes an annular channel formed by said skirt and said first portion, a distal edge portion of said housing received in said channel.

4. The connector device of claim 3 wherein said distal edge portion forms a distal landing received in said channel, at least a portion of said distal landing being attached to said septum.

5. The connector of claim 4 wherein the entire length of said landing is attached to said septum.

6. The connector device of claim 4 wherein said connector includes a bonding agent to attach said outside surface and said landing to said septum.

7. The connector device of claim 6 wherein said connector includes an amount of said bonding agent attaching said first portion to said housing being equal to or less than the amount of bonding agent found on an inside surface of said housing at said distal edge portion when said bonding agent is applied to said outside surface when said housing is oriented with said distal edge portion in a downward direction.

8. The connector device of claim 1 wherein said second portion of said resealable valve is formed with a generally rectangular cross section in the proximate direction.

9. The connector of claim 1 wherein said housing includes a distal edge portion having an outside surface of generally constant diameter, and a second portion extending proximately from said edge portion and having a generally frustoconical shape, said second portion being threaded for threadingly engaging the annular flange.

10. The connector device of claim 9 wherein the valve includes an annular skirt attached to said first portion, said skirt extending over and attached to said outside surface of said distal edge portion.

* * * * *